(12) United States Patent
Wampler

(10) Patent No.: US 6,234,998 B1
(45) Date of Patent: *May 22, 2001

(54) SEALLESS ROTARY BLOOD PUMP

(75) Inventor: Richard K. Wampler, Granite Bay, CA (US)

(73) Assignee: Kriton Medical, Inc., Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/420,997

(22) Filed: Oct. 20, 1999

Related U.S. Application Data

(60) Continuation of application No. 09/108,434, filed on Jul. 1, 1998, now Pat. No. 6,080,133, which is a division of application No. 08/910,375, filed on Aug. 13, 1997, now Pat. No. 5,840,070, which is a continuation-in-part of application No. 08/603,536, filed on Feb. 20, 1996, now Pat. No. 5,695,471.

(51) Int. Cl.[7] .................................................. A61M 37/00
(52) U.S. Cl. ............................................................ 604/131
(58) Field of Search ...................................... 604/131, 151; 417/423.1, 423.7, 423.12, 321, 203, 206

(56) References Cited

U.S. PATENT DOCUMENTS

| | | |
|---|---|---|
| 2,725,266 | 11/1955 | Mendelsohn . |
| 3,487,784 | 1/1970 | Rafferty et al. . |
| 3,493,274 | 2/1970 | Emslie et al. . |
| 3,957,389 | 5/1976 | Rafferty et al. . |
| 4,057,369 | 11/1977 | Isenberg et al. . |
| 4,072,370 | 2/1978 | Wasson . |
| 4,135,253 | 1/1979 | Reich et al. . |
| 4,253,798 | 3/1981 | Sugiura . |
| 4,382,245 | 5/1983 | Harrigan . |
| 4,507,048 | 3/1985 | Belenger et al. . |
| 4,625,712 | 12/1986 | Wampler . |
| 4,688,998 | 8/1987 | Olsen et al. . |
| 4,704,121 | 11/1987 | Moise . |
| 4,745,345 | 5/1988 | Petersen . |
| 4,763,032 | 8/1988 | Bramm et al. . |
| 4,779,614 | 10/1988 | Moise . |
| 4,789,251 | 12/1988 | McPherson et al. . |
| 4,806,080 | 2/1989 | Mizobuchi et al. . |
| 4,846,152 | 7/1989 | Wampler et al. . |

(List continued on next page.)

Primary Examiner—Sharon Kennedy
Assistant Examiner—Ann Y. Lam
(74) Attorney, Agent, or Firm—George H. Gerstman; Seyfarth Shaw

(57) ABSTRACT

A implantable rotary sealless blood pump is provided. The pump includes a housing having an inlet tube on one end and an impeller casing on the other end. A rotor is mounted for rotation within the housing, with the rotor having an elongated shaft portion and an impeller attached to the shaft portion. The impeller is located within the impeller casing. Radial magnetic bearings are carried by the shaft portion and radial magnetic bearings are carried by the housing for maintaining the shaft portion of the rotor within the inlet tube of the housing. A rotor motor includes a plurality of permanent magnets carried by the impeller and a motor stator including an electrically conductive coil located within the housing. A ring of back iron is carried by the impeller to aid in completing a flux return path for the permanent magnets. A plurality of hydrodynamic thrust bearings are located outside of the axis of rotation of the rotor. The impeller uses large axially thick blade sectors with narrow blood channels extending through the impeller, to minimize hemolysis and to increase the working surface of the blades.

32 Claims, 13 Drawing Sheets

U.S. PATENT DOCUMENTS

| | | |
|---|---|---|
| 4,908,012 | 3/1990 | Moise et al. . |
| 4,944,748 | 7/1990 | Bramm et al. . |
| 4,957,504 | 9/1990 | Chardack . |
| 4,976,729 | 12/1990 | Holfert et al. . |
| 4,994,017 | 2/1991 | Yozu . |
| 4,994,078 | 2/1991 | Jarvik . |
| 5,017,103 | 5/1991 | Dahl . |
| 5,049,134 | 9/1991 | Golding et al. . |
| 5,055,005 | 10/1991 | Kletschka . |
| 5,078,741 | 1/1992 | Bramm et al. . |
| 5,092,879 | 3/1992 | Jarvik . |
| 5,106,263 | 4/1992 | Irie . |
| 5,112,200 | 5/1992 | Isaacson et al. . |
| 5,112,202 | 5/1992 | Oshima et al. . |
| 5,147,388 | 9/1992 | Yamazaki . |
| 5,149,253 | 9/1992 | Miyamoto et al. . |
| 5,160,246 | 11/1992 | Horiuchi . |
| 5,182,533 | 1/1993 | Ritts . |
| 5,195,877 | 3/1993 | Kletschka . |
| 5,201,642 | 4/1993 | Hinckley . |
| 5,211,546 | 5/1993 | Isaacson et al. . |
| 5,282,849 | 2/1994 | Kolff et al. . |
| 5,290,236 | 3/1994 | Mathewson . |
| 5,302,091 | 4/1994 | Horiuchi . |
| 5,306,295 | 4/1994 | Kolff et al. . |
| 5,316,440 | 5/1994 | Kijima et al. . |
| 5,324,177 | 6/1994 | Golding et al. . |
| 5,342,825 | 8/1994 | Iannello et al. . |
| 5,370,509 | 12/1994 | Golding et al. . |
| 5,385,581 | 1/1995 | Bramm et al. . |
| 5,392,881 | 2/1995 | Cho et al. . |
| 5,397,349 | 3/1995 | Kolff et al. . |
| 5,397,953 | 3/1995 | Cho . |
| 5,399,074 | 3/1995 | Nose et al. . |
| 5,405,251 * | 4/1995 | Sipin ................... 417/420 |
| 5,441,535 | 8/1995 | Takahashi et al. . |
| 5,443,503 | 8/1995 | Yamane . |
| 5,470,208 | 11/1995 | Kletschka . |
| 5,507,629 | 4/1996 | Jarvik . |
| 5,527,159 | 6/1996 | Bozeman, Jr. et al. . |
| 5,569,111 | 10/1996 | Cho et al. . |
| 5,575,630 | 11/1996 | Nakazawa et al. . |
| 5,588,812 | 12/1996 | Taylor et al. . |
| 5,601,418 | 2/1997 | Ohara et al. . |
| 5,607,329 | 3/1997 | Cho et al. . |
| 5,613,935 | 3/1997 | Jarvik . |
| 5,649,811 | 7/1997 | Krol, Jr. et al. . |
| 5,678,306 * | 10/1997 | Bozeman, Jr. et al. ........ 29/888.025 |
| 5,695,471 | 12/1997 | Wampler . |
| 5,746,575 | 5/1998 | Westphal et al. . |
| 5,840,070 * | 11/1998 | Wampler ............... 604/131 |

* cited by examiner

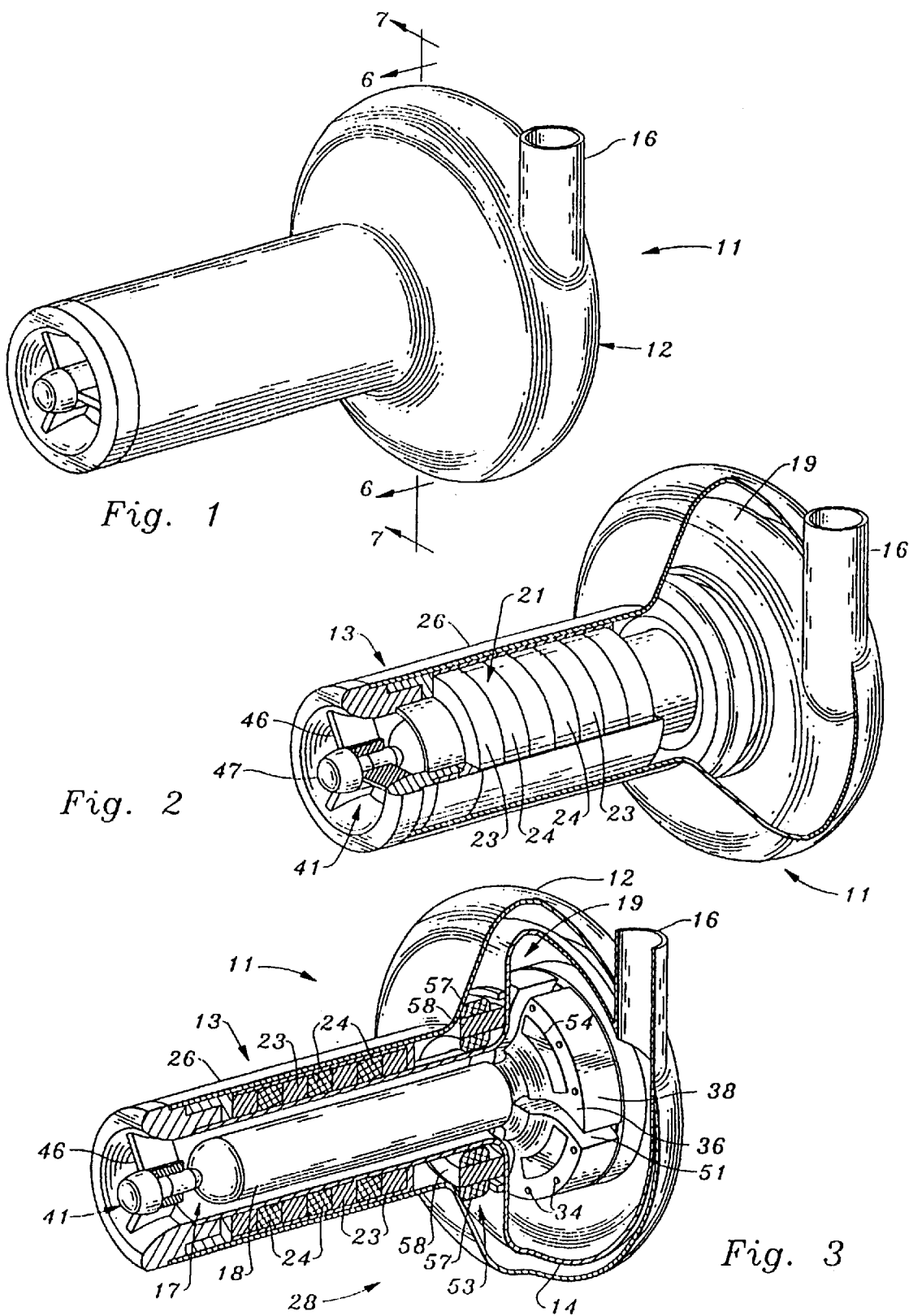

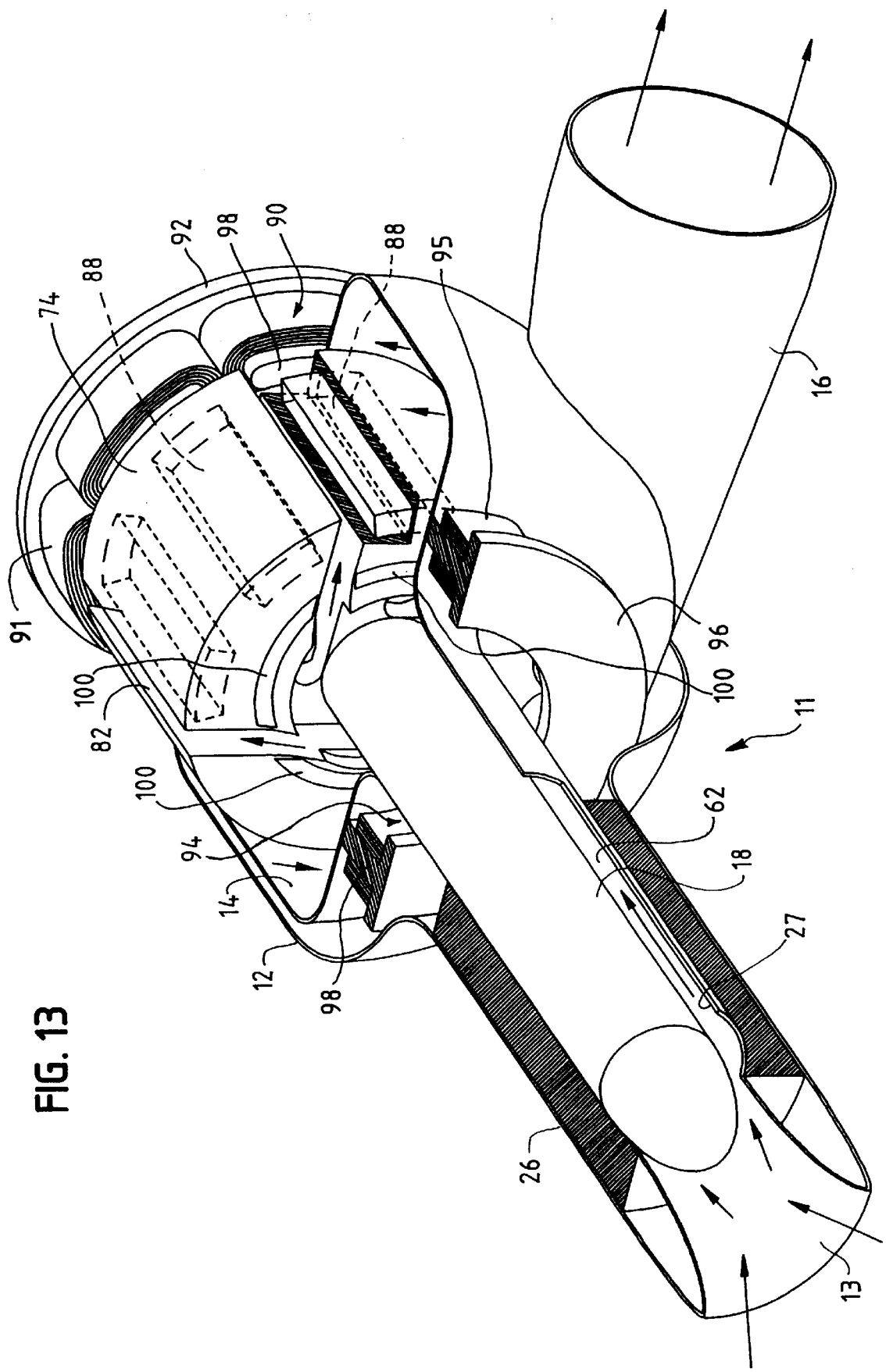

SEALLESS ROTARY BLOOD PUMP

This application is a continuation of U.S. application Ser. No. 09/108,434, filed Jul. 1, 1998, now U.S. Pat. No. 6,080,133, which is a division of U.S. application Ser. No. 08/910,375, filed Aug. 13, 1997, now U.S. Pat. No. 5,840,070, which is a continuation-in-part of U.S. application Ser. No. 08/603,536, filed Feb. 20, 1996, now U.S. Pat. No. 5,695,471.

FIELD OF THE INVENTION

The invention relates generally to the field of blood pumps. More specifically, the invention pertains to continuous flow pumps of rotary design, suitable for permanent implantation in humans, for use as chronic ventricular assist devices.

BACKGROUND OF THE INVENTION

Thousands of heart patients who suffer from severe left ventricular heart failure could benefit from cardiac transplantation. However, owing to a shortage of donor hearts, most of these patients face a foreshortened life span characterized by frequent hospitalizations, severe physical disability, and death from congestive failure or cardiogenic shock. If a left ventricular assist device ("LVAD") were available for chronic use, many of these patients could be returned to prolonged and productive lives.

Prior art LVADs, now in clinical trials, provide a cyclic or pulsating delivery of blood, designed to emulate the natural pulsatile blood flow through the heart. This design approach has resulted in a variety of anatomic and engineering problems. Cyclic delivery systems tend to be physically large, making implantation difficult or impossible for some patients. Cyclic delivery systems also employ artificial valves, having special material, longevity, and performance requirements. All of these characteristics make cyclic blood pumping devices both complex and expensive.

It is apparent that if the requirement of pulsatile blood flow is eliminated, the LVAD could be much smaller, simpler, and less expensive. Rotary pumps, whether of centrifugal or axial flow design, provide substantially continuous liquid flow, and potentially enjoy a number of the listed advantages over cyclic delivery systems. However, the prior art has not developed a durable rotary blood pump, owing to unique problems with the rotary pump's driveshaft seal. In a blood environment, such driveshaft seals have a short life, and contribute to a premature failure of the pump. Prior art driveshaft seals may also cause embolisms, resulting in a stroke or even death for the patient.

Accordingly, it is an object of the present invention to provide an improved rotary blood pump, by eliminating the necessity for a driveshaft seal;

It is a further object of the present invention to provide a compact, rotary blood pump using passive, magnetic radial bearings to maintain an impeller and its support shaft for rotation about an axis;

It is yet a further object of the present invention to provide a rotary blood pump having bi-stable operation, in which the impeller and the support shaft shuttle as a unit, between two predetermined axial positions;

It is another object of the present invention to provide blood immersed axial thrust bearings which are regularly washed by fresh blood flow to prevent thrombosis from occurring;

It is yet another object of the present invention to provide a unique thick bladed pump impeller, which houses both motor magnets and radial bearing magnets, and includes narrow, deep, blood flow passages;

It is yet another object of the present invention to provide a pump impeller which is effective pumping viscous liquids, such as blood, at low flow rates, and which minimizes hemolysis of the blood by using only a few pump impeller blades.

SUMMARY OF THE INVENTION

In accordance with illustrative embodiments of the present invention, a rotary blood pump includes a housing and a pump rotor. A centrifugal pump impeller is attached to an impeller support shaft, or spindle, to form the pump rotor. The pump housing includes an elongated inlet tube surrounding the shaft, and a scroll-shaped casing, or volute, with a discharge outlet, enclosing the impeller.

The shaft and the impeller are specially suspended within the housing. Radial magnetic bearings of passive design, maintain the support shaft and the impeller about a rotational axis. The magnetic bearing which levitates the shaft includes a plurality of permanent ring magnets and pole pieces arranged along surrounding portions of the inlet tube, and a plurality of permanent disc magnets and pole pieces within the shaft itself. Radially adjacent pairs of these magnets are of like polarity. One part of the magnetic bearing, which maintains the impeller about a rotational axis, includes a plurality of permanent rod or arcuate magnets disposed in spaced, circular relation around blade sectors of the impeller; another part of the bearing includes a pair of permanent ring magnets outside the casing, on either side of the impeller. Adjacent portions of the rod and ring magnets are of opposite polarity.

The shaft and impeller are axially restrained by a magnetic and hydrodynamic forces in combination with mechanical thrust bearings, or touchdowns. The magnets of the magnetic bearing in the inlet tube and shaft may be arranged in slightly offset axial relation, to produce a translational loading force, or bias, along the longitudinal axis of the rotor. This bias substantially counteracts the axial force resulting from the hydraulic thrust of the rotating impeller. However, the hydraulic thrust will vary as a function of the cardiac cycle and additional restraints are desirable to ensure that pump operation is stable and controlled. For this purpose, a pair of blood immersed thrust bearings is provided. These thrust bearings may be located at either end of the rotor, although other arrangements are feasible.

One thrust bearing is included at the upstream end of the support shaft, and the other thrust bearing is located on the bottom, or downstream side of the impeller. A spider within the inlet tube includes a touchdown, or thrust surface, against which the end of the shaft periodically touches. Another touchdown is provided on an inner surface of the casing base, adjacent a downstream terminus of the impeller. A predetermined amount of spacing is included between the two touchdowns, so as to allow the shaft/impeller assembly axially to shuttle back and forth, in response to the user's cardiac cycle. This shuttling motion will produce a pumping action, frequently exchanging blood in the touchdown area with fresh blood from the circulation. This pumping action minimizes the likelihood of blood thrombosis in the thrust region, by maintaining the blood at an acceptable temperature and by shortening its residence time in the thrust bearing gap.

The impeller is of unique configuration and characteristics, owing to the special requirements of the present application. Contrary to conventional centrifugal pump design, the present invention uses relatively few impeller blades, generally resembling pie-shaped sectors. Moreover, the blades are made quite thick in an axial direction, having deep and narrow, arcuate channels between adjacent blades for the passage of blood through the impeller. The substantial height of the blades provides a relatively large blade working surface, ensuring efficient pump operation. These structural features decrease hemolysis of the blood, while maintaining useful efficiency in a pump using so few impeller blades.

Sealed, hollow chambers are provided within the thick impeller blades to reduce the density of the impeller. These chambers reduce gravity induced loads on the thrust bearings, which in turn reduces the likelihood of thrombosis of the blood used to lubricate the bearings.

The thick impeller blades are also used advantageously to house magnets used in the pump drive system. Torque drive is imparted to the impeller by magnetic interaction between arcuate, permanent magnetic segments imbedded within each impeller blade sector, and a circular electromagnetic stator, affixed to the casing. Back-EMF sensing is used to commutate the brushless motor stator, providing attractive and repulsive forces upon the magnetic segments. A control unit and a portable power supply, worn on the user, power the pump drive system. The control unit allows the speed and drive cycle of the motor either to be programmed or interactively determined by the user's physical activity or condition.

In certain embodiments of the invention, the motor includes a plurality of permanent magnets carried by the impeller and a motor stator including an electrically conductive coil located within the housing. A ring of back iron is fixed to the casing to aid in completing a flux return path for the permanent magnets and to decrease the axial thrust which results from the attraction of the motor rotor magnets toward the motor rotor stator. The impeller has a forward side facing the inlet tube and a rear side downstream of the forward side. In one embodiment, the conductive coil of the motor stator is located adjacent the rear side of the impeller, and a stator back iron ring is located outside of the conductive coil, within the housing and fixed to the housing. In one embodiment, a second ring of back iron is located on the forward side of the impeller and outside of the casing but inside of the housing, with the second ring of back iron being fixed to the casing. In that embodiment, a second motor stator having an electrically conductive coil is located on the forward side of the impeller outside of the casing but inside of the housing. In that embodiment, the second ring of back iron is located forward of the second motor stator.

In certain embodiments, a plurality of hydrodynamic thrust bearings are located outside of the axis of rotation of the rotor. The hydrodynamic bearings are wedge-shaped and, during rotation of the rotor and impeller, the hydrodynamic bearings are separated from the casing by a fluid film and are not in direct mechanical contact with the casing.

A more detailed explanation of the invention is provided in the following description and claims, and is illustrated in the accompanying drawings.

BRIEF DESCRIPTION OF THE DRAWINGS

FIG. 1 is a left front perspective of the blood pump of the present invention;

FIG. 2 is a fragmentary, cross-sectional view of the pump of FIG. 1, showing a plurality of ring magnets comprising part of the magnetic bearing assembly;

FIG. 3 is a fragmentary, cross-sectional view of the pump of FIG. 1, showing the shaft and an impeller;

FIG. 13 is a perspective view, partially broken for clarity, of the blood pump of FIG. 11;

DETAILED DESCRIPTION OF THE PREFERRED EMBODIMENT

Figure 4:
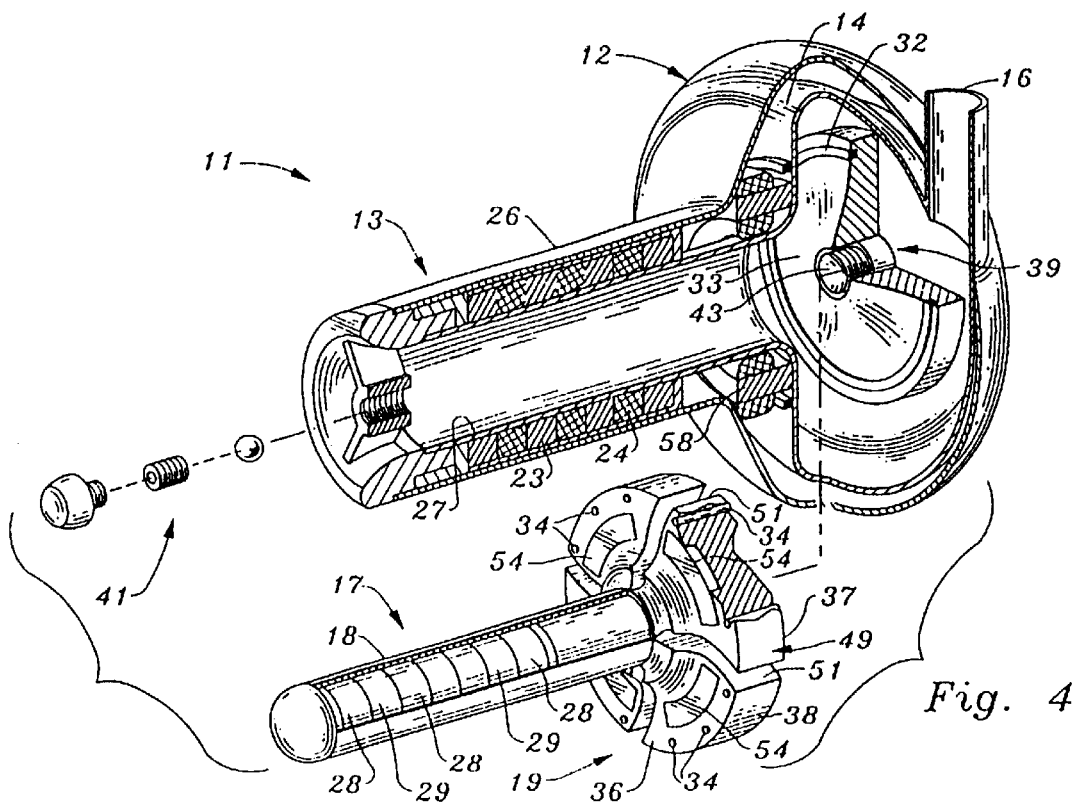
FIG. 4 is a view as in FIG. 1, but with the shaft and impeller shown removed from the housing.

Turing now to FIGS. 1–8 of the drawings, a sealless rotary blood pump 11 includes a housing 12, having an elongated inlet tube 13 and an impeller casing or volute 14. A discharge tube 16 extends through the housing to communicate with the interior periphery of casing 14. Tube 16 has a tangential orientation with respect to a radius of the casing, for effectively channeling the blood output from the pump.

A pump rotor 17 is located within housing 12, within casing 14, and includes an elongated, right-circular cylindrical support shaft or spindle 18, attached to a disc-shaped impeller 19. Rotor 17 is mounted for rotation about a longitudinal axis which extends both through shaft 18 and impeller 19. It should be noted that the preferred embodiment disclosed herein includes an impeller and a casing of centrifugal design. However, many of the structural features and aspects of operation of the present invention may also be adapted advantageously to rotary blood pumps of axial flow design.

The pump 11 of the present invention includes a forward magnetic bearing 21 and a rearward magnetic bearing 22 to levitate rotor 17 and maintain it in proper radial alignment with respect to its longitudinal axis. A radial magnetic bearing construction is shown in U.S. Pat. No. 4,072,370, issued to Wasson. The '370 patent is hereby expressly incorporated by reference. The forward magnetic bearing 21 herein may be constructed entirely in accordance with the teachings of the '370 patent. However, several simplifications and improvements to the construction shown in the '370 patent are disclosed herein. For example, it has been determined that the radially polarized ring magnets (numerals 44 and 46) of the '370 device, are not necessary for successful practice of the invention herein. In addition, as will be explained below, the axially magnetized ring magnets (numeral 22) of the '370 device may advantageously be replaced with axially magnetized disc magnets for purposes of the present invention.

Accordingly, the forward magnetic bearing 21 includes a plurality of rings, comprising ferromagnetic pole pieces 23 and axially polarized permanent magnets 24. As shown most clearly in FIGS. 7 and 8, pole pieces 23 and magnets 24 are arranged in contingent, alternating fashion, and are located between outer sidewall 26 and inner sidewall 27 of inlet tube 13. The polarization of opposing magnets is the same, inducing an identical polarization into a respective pole piece therebetween. A combination of high strength adhesive and surrounding tube sidewalls, maintains the arrangement of magnets and pole pieces in contingent relation, despite strong magnet forces attempting to urge the rings apart.

Forward magnetic bearing 21 also includes a plurality of discs, comprising ferromagnetic pole pieces 28 and axially polarized permanent magnets 29. Pole pieces 28 and magnets 29 are also arranged in contingent, alternating fashion, so as to form a magnetic structure which mirrors the polarity and axial position of respective pieces and magnets of the surrounding rings. This magnetic structure is first assembled and secured together using high strength adhesive, and is then installed within the hollow volume of shaft or spindle 17. The magnetic polarizations and repulsive forces produced by the magnets and the pole pieces of forward magnetic bearing 21 are such that magnetic levitation of support shaft 18 results.

To provide additional radial restraint for rotor 17, rearward magnetic bearing 22 is also provided. Bearing 22 includes a first ring magnet 31 mounted on an outer wall of casing 14, and a second ring magnet 32 imbedded within a circular casing base 33. The bottom portion of casing 14 is attached and sealed to base 33, to form a fluid impervious enclosure for impeller 19 (see FIG. 7). Both magnets 31 and 32 are axially polarized, but each has a different polarization facing impeller 19. Bearing 22 also includes a plurality of rod magnets 34, transversely extending from an upper face portion 36 to a lower face portion 37 of impeller 19. Rod magnets 34 are arranged in spaced, circular fashion, adjacent an outer periphery 38 of impeller 19. The polarizations between the ends of magnets 34 and the adjacent surfaces of magnets 31 and 32 are respectively opposite, creating attractive, but equal and opposite magnetic forces acting on the impeller. It can be seen that radial movement of the impeller (deflection from the axis of rotation) will result in a restoring force due to the attraction between the magnets 34 towards magnets 31 and 32. The magnetic force in the axial direction will largely be counterbalanced to the opposing magnetic attraction of magnets 34 to magnet 31 and magnets 34 to magnet 32. However, the action of the magnetic force in the axial direction would not be restoring.

Figure 8:
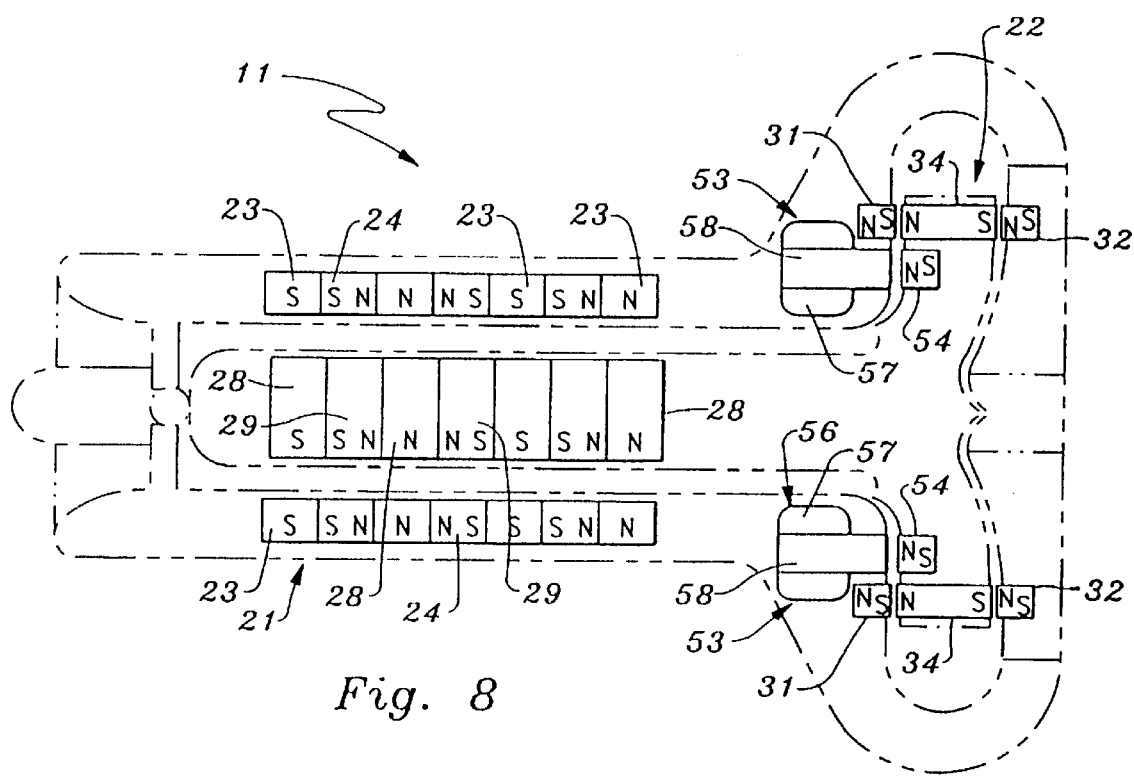
FIG. 8 is a longitudinal, cross-sectional view of a simplified, schematic representation of the pump, showing respective polarities of the magnets and the pole pieces of the passive radial magnetic bearings, and the elements of the pump motor, including rotor magnets and a motor stator.
Figure 8A:
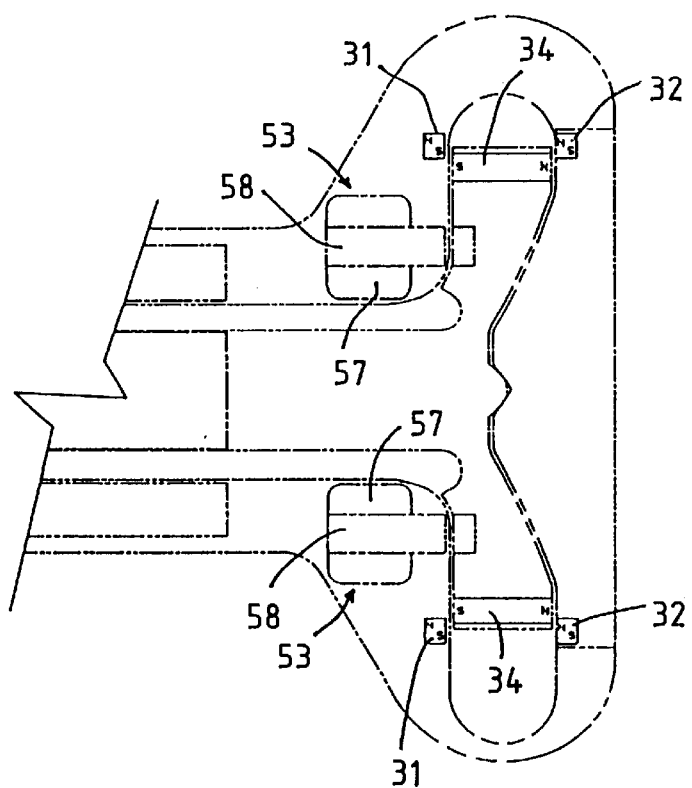
FIG. 8a is a schematic view, similar to FIG. 8, but showing another embodiment of the present invention.
Figure 8B:
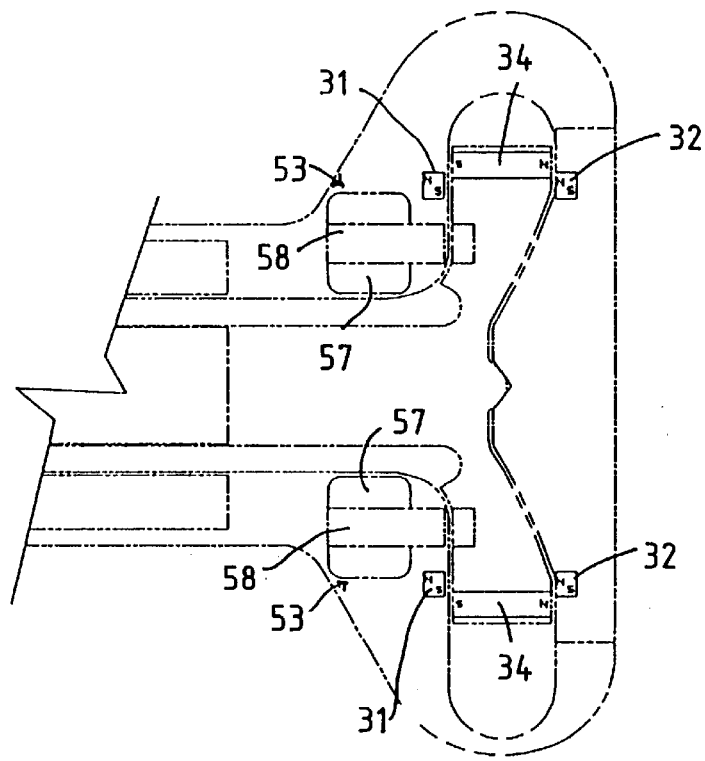
FIG. 8b is a schematic view, similar to FIG. 8a, but showing another embodiment of the present invention.

It should also be noted that other configurations, locations, numbers, and polarization orientations may be used for the components forming rearward magnetic bearing 22. For example, magnets 34 may be arcuate segments, rather than rods. Also, the polarizations of the magnets 31, 32, and 34 may be arranged to effect respective repulsive forces, rather than the attractive forces specifically disclosed herein. In this manner, referring to FIGS. 8a and 8b, the south pole of magnets 34 would be adjacent the south pole of magnet 31 and the north pole of magnets 34 would be adjacent the north pole of magnet 32. For the magnets to be restoring in the radial direction, the magnets would have to be offset. To this end, in the FIG. 8a embodiment magnets 34 would be more outward radially than magnets 31 and 32. Alternatively, in the FIG. 8b embodiment magnets 34 are radially inside the radial dimension of magnets 31 and 32. If a repulsive configuration is used, as illustrated in FIGS. 8a and 8b, the action of the magnetic force would be restoring in both the radial and axial direction.

Although the drawings show magnets 32 and 34 as if portions thereof are directly immersed in blood, in actual practice, a thin-walled non-magnetic jacket or a plastic coating would be placed over these portions, to prevent contact between the magnets and the blood. Such contact, if it were allowed, would likely cause an undesirable chemical reaction, to the detriment of the blood. However, for clarity, the referenced jacket or coating, is not shown in the drawings.

To provide mechanical limitations on axial, translational excursions of the rotor, a first thrust bearing 39 and a second thrust bearing 41 are provided. First thrust bearing 39 includes a threaded plug 42, installed within casing base 33. Plug 42 is screw adjustable along the longitudinal axis of rotor 17, and includes a recessed bearing surface 43. Surface 43 is contoured to accommodate a corresponding bearing tip 44, in the lower face portion of impeller 19. It should be noted that the particular configuration of bearing 39 is not critical, and planar bearing surfaces may alternatively be used in this application.

Second thrust bearing 41 is secured within the blood entry end of inlet tube 13, and includes a spider 46, adjustment knob 47, and ball 48. Rotation of knob 47 will translate ball 48 along the longitudinal axis of rotor 17.

Alternative locations and constructions for second thrust bearing 41 are also contemplated. For example, an annular thrust bearing surface could be provided on the inner wall of casing 14, adjacent the upper face portion 36 of impeller 19. In this arrangement, portion 36 would slidably contact the annular thrust bearing surface. By eliminating spider 46 and the associated components of the upstream thrust bearing, the possibility of blood deposits forming on these structures would be eliminated.

It will be appreciated that thrust bearings 39 and 41 are effective not only to provide limit stops to axial movement of rotor 17, but also to adjust certain operational aspects of the pump. In the drawings, the upstream end of support shaft 18 is shown in contact with ball 48. However, this will not always be the case during the course of operating the pump. For example, it is desirable for the two thrust bearings to be adjusted so that the distance between them, is slightly greater than the overall length of the rotor. This will allow the rotor to "shuttle", back and forth between the axial constraints provided by the thrust bearings with each cardiac cycle of the user. Each such cycle will produce a pumping action, bringing fresh blood into the touchdown, or thrust bearing area.

The present invention does not use a journal bearing to restrain the rotor. Of necessity, a journal bearing radially encases at least a portion of the rotor's support shaft or spindle. It is within this thin, annular volume between the shaft and the bearing surface, where thrombosis can occur in prior art devices as a consequence of heat and excessive residence time within the bearing. The bi-stable operation of the pump and rotor of the present invention, continuously flushes the blood around each thrust bearing, avoiding thrombosis effects of prior art journal bearings.

There is also an important physical relationship which exists between the rotor and the magnetic bearings of the device disclosed herein. This relationship is established and maintained by proper axial placement of the adjustable thrust bearings. In operation of the pump, the pressure gradient produced by the rotating impeller imparts an upstream axial force on the rotor. This force needs to be substantially counterbalanced, to ensure that cardiac pulses will create sufficient pressure variances through the pump, to effect bi-stable operation. By adjusting the axial relationship of the pole pieces 23 and the magnets 24 with respect to the pole pieces 28 and magnets 29, a downstream axial force will be produced. Since the forces within forward magnetic bearing 21 are repulsive, the desired downstream loading or bias will be effected when the magnets and pole pieces within the shaft are translated slightly downstream from the magnets and pole pieces in the inlet tube (See, FIGS. 7 and 8). Thus, second thrust bearing 41 is effective to shift, or offset the rotor downstream a sufficient amount so the resultant, repulsive magnetic forces substantially counterbalance the hydrodynamic axial force produced by the rotating pump impeller.

We can now turn to the special design considerations and operational characteristics of impeller 19. As will be noted particularly in FIG. 6, the impeller includes a plurality of large blade sectors 49. Owing to its relatively high viscosity and susceptibility to damage from heat and mechanical action, blood is a uniquely difficult liquid to pump.

It is generally preferable in a large centrifugal pump, to have a substantial number of thin, sharp impeller blades with relatively large voids or passages, between the blades, for the passage of low viscosity liquid. However, such a conventional design is not desirable, for a small centrifugal pump which has to pump a viscous liquid, such as blood.

When blood flows axially into the leading edges of impeller blades it tends to be damaged by the mechanical action and turbulence associated with the impeller blades. Thus, one of the design considerations of the present invention is to reduce such hemolysis, by minimizing the number of impeller blades and leading edges.

To maintain efficiency in a small pump with so few blades, the effective working area of the blades needs to be increased. This was accomplished in the present design by modifying the size and configuration of conventional blades in two significant aspects. First, blade sectors 49 are made relatively wide or expansive through a rotational aspect (see FIG. 6). In other words, the outer periphery of each blade sector 49 assumes approximately 80 to 85 degrees of rotation. It should be noted that an alternative design contemplated herein includes only two blade sectors, each of which assumes approximately 175 degrees of rotation. In either case, the width of the impeller blade sectors of the present invention differ significantly from known prior art blades.

The second modification pertains to the thickness or height of the blade sectors. As shown particularly in FIGS. 4 and 7, blade sectors 49 are relatively thick in an axial direction. As a consequence of these modifications, a narrow and deep impeller blood flow path or passageway 51 is defined between adjacent edges of blade sectors 49. By increasing the thickness of the blade sectors and narrowing the blood passageway, the ratio between the area of working surface of the blades and the volume of the passageway is increased. Also, the average distance of the liquid in the passageway from the working surface of the blades is decreased. Both of these beneficial results provide a small pump for blood which has few blades for damaging blood, yet maintains acceptable efficiency.

The size and configuration of the impeller blades also allows the structural integration of a number of features directly within the impeller 19. For example, the previously discussed rearward magnetic bearing 22 includes a plurality of rod magnets 34 of considerable length. Owing to the thickness of the blade sectors, these magnets are readily accommodated within the sectors. The sectors may also be provided with respective hollow chambers 52, to reduce the mass of the impeller and the gravity induced loads on the thrust bearings (see, FIG. 6).

Figure 5:
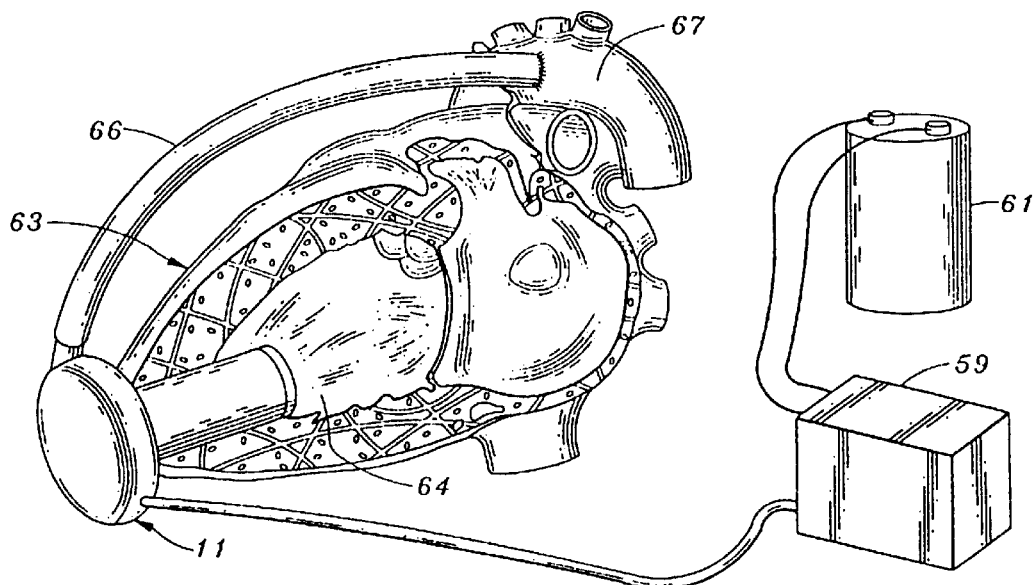
FIG. 5 is a simplified, fragmentary, representation of a human heart, showing the pump implanted within the left ventricle of the heart.
Figure 6:
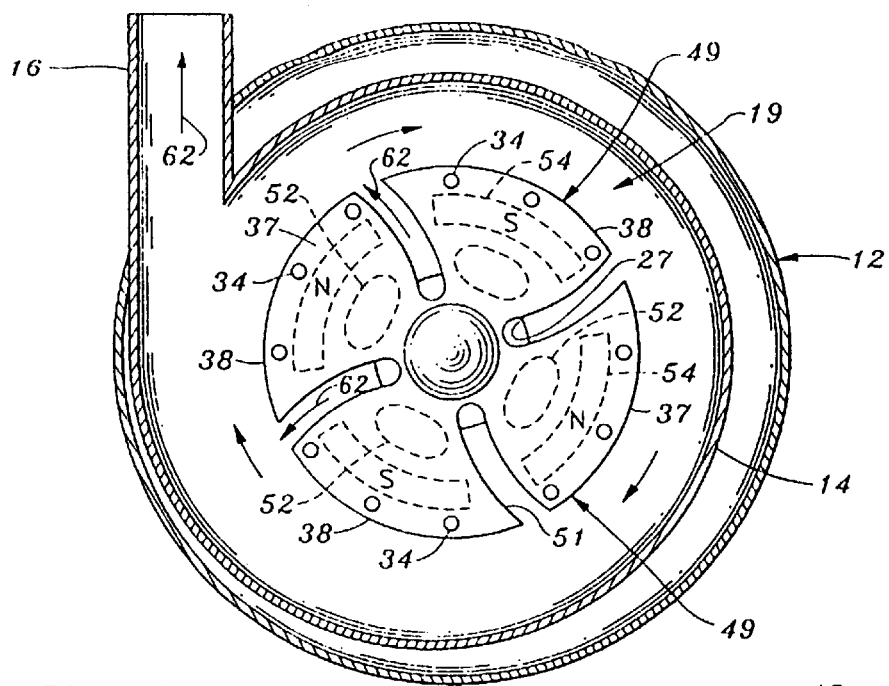
FIG. 6 is a transverse, cross-sectional view of the housing, impeller, and impeller chamber, taken along the line 6—6, shown in FIG. 1.

Lastly, a brushless rotor motor 53 includes arcuate magnetic segments 54, imbedded within the upper face portion 36 of blade sectors 49. As discussed above, the portions of segments 54 which would otherwise be in fluid communication with the pumped blood, are encased in a jacket or a coating (not shown) to prevent any chemical reaction between the blood and the magnetic segments. Making reference to FIGS. 6 and 8, segments 54 have alternating orientations in their polarities, and are directed toward an adjacent motor stator 56. Included within stator 56 are windings 57 and a circular pole piece or back iron 58, mounted on the outer surface of impeller casing 14. Windings 57 are interconnected by means of percutaneous wires to a controller 59 and a power supply 61, as shown in FIG. 5. Alternative to using wires, transcutaneous power transmission could be used. It is contemplated that controller 59 and power supply 61 may be worn externally by the user, or alternatively, they may be completely implanted in the user.

Controller 59 may include circuitry as simple as a variable voltage or current control, manually adjusted or programmed to determine the running rate of pump. However, controller 59 may also have interactive and automatic capabilities. For example, controller 59 may be interconnected to sensors on various organs of the user, automatically and instantaneously to tailor operation of the pump to the user's physical activity and condition.

The windings 57 are energized by the electrical output of controller 59 to produce an electromagnetic field. This field is concentrated by pole piece 58, and is effective to drive magnets 54 and the rotor 17, in rotary fashion. The back EMF resulting from the magnets 54 passing by the windings is detected by the controller. The controller uses this back EMF voltage to continue generation of the electromagnetic field in synchronism with further rotation of the rotor. Brushless operation of the motor 53 is effected, then, by electromagnetic interaction between the stator and magnets imbedded within the pump's impeller blades.

Figure 7:
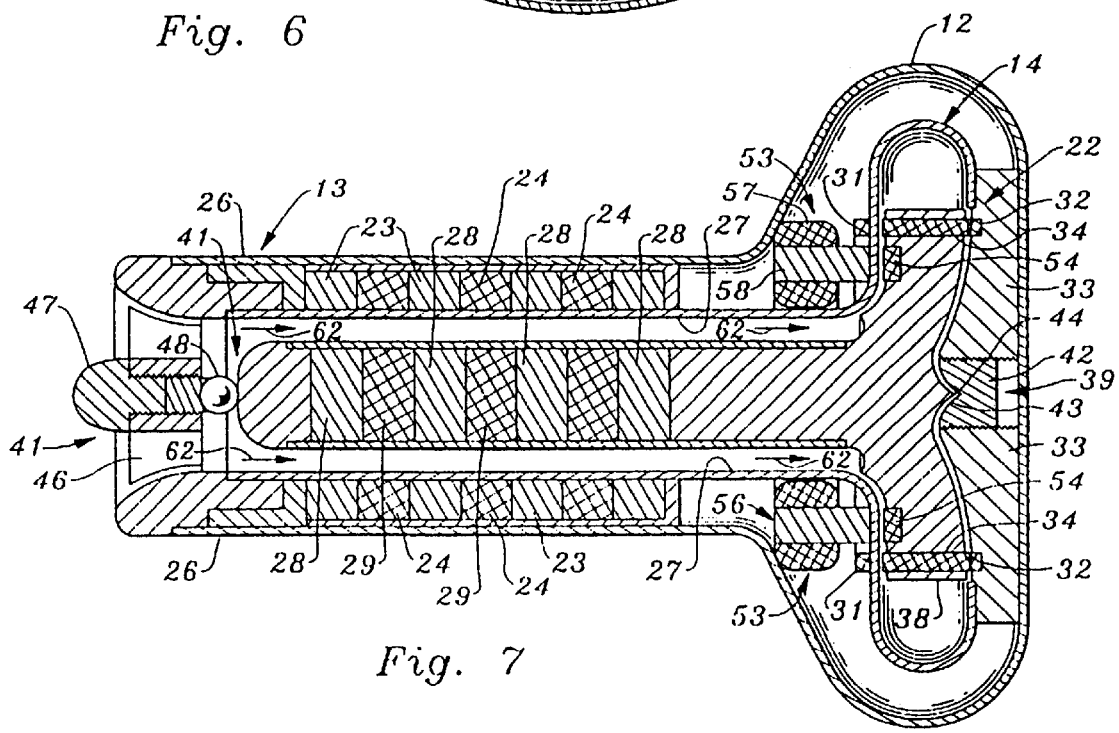
FIG. 7 is a longitudinal, cross-sectional view of the pump, taken along the line 7–7, shown in FIG. 1.

Motor 53, with windings 57 and pole piece 58, together with magnets 54, function not only to transmit torque but also provide a restoring radial magnetic force that acts as a radial bearing. As illustrated in FIGS. 7 and 8, magnets 54 are carried by blade sectors 49 and are positioned in radial alignment with pole piece 58. The magnets 54 have attraction with the iron pole piece 58 of the stator. Any attempt to deflect the impeller radially produces an increasing restoring force between the pole piece 58 and the magnets 54 which would cause the impeller to return to a neutral position.

Rotation of the rotor 17, including shaft 18 and impeller 19, causes blood to flow through inlet tube 13 in the direction of arrows 62. The blood continues its path from the upper edge of passage 51 to the interior of casing 14. Discharge tube 16 allows the blood to be expelled from the casing an into the user's cardiovascular system.

Anatomical placement of the pump 11 is shown in FIG. 5. The simplified representation of a human heart 63, includes a left ventricle 64 and an aorta 67. The inlet tube 16 serves as the inflow cannula and is placed into the apex of the left ventricle 64. An arterial vascular graft 66 is connected on one end to tube 16 and on the other end to the aorta 67 through an end to side anastomosis.

The centrifugal design of the pump allows a considerable amount of flexibility during implantation. Owing to the axial inflow and radial outflow of the pump, a 90 degree redirection of the blood is effected without the necessity of a flow-restrictive elbow fitting. Moreover, the pump can be rotated on its longitudinal axis to adjust the orientation of the discharge tube and minimize kinking and hydraulic losses in the vascular graft. Good anatomic compatibility is possible since the pump casing is compact and disc-shaped, fitting well between the apex of the heart and the adjacent diaphragm.

In a specific example although no limitation is intended, referring to FIG. 7, blood flow path 62a is 0.06 inch to 0.1 inch in thickness. The fluid gap 70 comprising the clearance between the impeller and the housing is 0.005 inch to 0.02 inch. The impeller diameter is 1.0 inch to 1.5 inch. The rotor diameter is 0.025 inch to 0.4 inch. The outside diameter of the flow annulus is 0.35 inch to 0.55 inch. The outer diameter of the housing adjacent the forward end of the pump is 0.85 inch to 1.25 inch. The axial length of the entire pump is 1.75 inch to 3.0 inch. The axial length of the rotor spindle is 1.0 inch to 1.5 inch and the axial length of the impeller is 0.2 inch to 0.5 inch. By using a thick impeller (having a long axial length) the fluid gap 70 can be larger and still provide a highly efficient pumping action.

Figure 9:
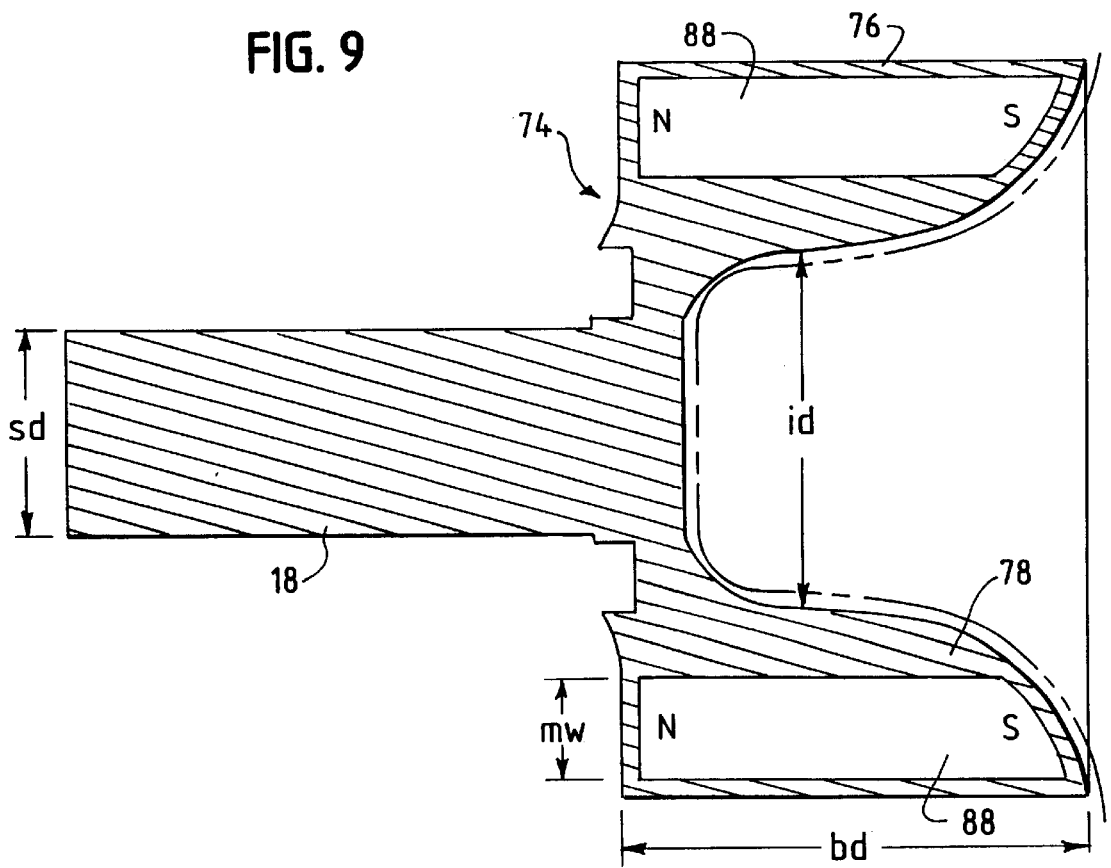
FIG. 9 is a longitudinal, cross-sectional view of an impeller constructed in accordance with the principles of the present invention.
Figure 10:
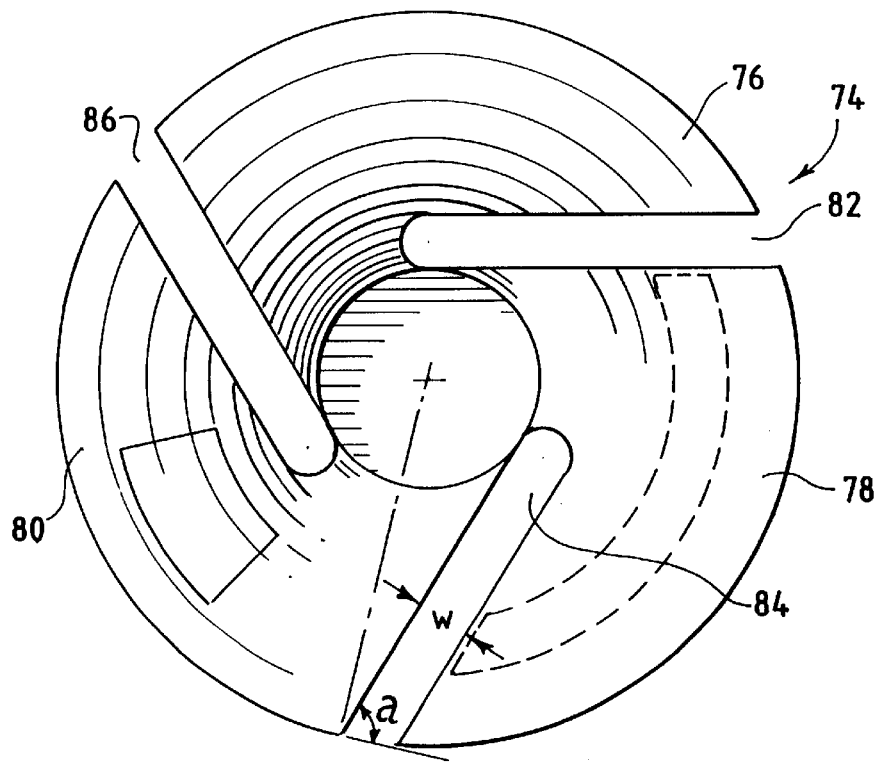
FIG. 10 is an end view thereof, taken from the right side of FIG. 9.

Enlarged views of an impeller used in the pump of the present invention are set forth in FIGS. 9 and 10. Referring to FIGS. 9 and 10, an impeller 74 is shown therein having a number of blade sectors 76, 78 and 80. Blade sectors 76 and 78 are separated by slot 82; blade sectors 78 and 80 are separated by slot 84; and blade sectors 80 and 76 are separated by slot 86. By utilizing blade sectors 76, 78 and 80 that are relatively thick in the axial direction, narrow and deep impeller blood flow paths are formed by slots 82, 84 and 86 between the adjacent edges of the blade sectors. By increasing the thickness of the blade sectors and narrowing the blood passageway, the ratio between the area of working surface of the blades and the volume of the passageway is increased. Also, the average distance of the liquid in the passageway from the working surface of the blades is decreased. Both of these beneficial results allow a small pump for blood which has less blades for potentially damaging blood, yet the small pump maintains acceptable efficiency.

As a specific example although no limitation is intended, the diameter of the impeller is 1 inch to 1.5 inch, the blade depth bd (FIG. 9) is 0.2 inch to 0.5 inch, the magnet width mw (FIG. 9) is 0.15 inch to 0.3 inch, the spindle diameter sd (FIG. 9) is 0.25 inch to 0.5 inch, and the inner diameter id (FIG. 9) of the impeller inlet is 0.45 inch to 0.6 inch. The width w of the slots (see FIG. 10) is approximately 0.075 inch and preferably ranges from 0.05 inch to 0.2 inch. The outlet angle a (FIG. 10) preferably between 30° and 90°.

Another benefit of the thick impeller is the ability to utilize magnetic pieces 88 that are inserted in a manner enabling the stators to be on opposite sides of the impeller. Referring to FIGS. 11, 11a, 12, 13 and 14, the blood pump 11' shown therein is similar in many respects to blood pump 11 illustrated in FIGS. 1–8, and includes housing 12 having an elongated inlet tube 13 and a scroll-shaped impeller casing or volute 14. A discharge tube 16 extends through the housing to communicate with the interior periphery of casing 14. Tube 16 has a tangential orientation with respect to a radius of the casing, for effectively channeling the blood output from the pump.

Pump rotor 17 is located within housing 12, within casing 14, and includes an elongated, right-circular cylindrical support shaft or spindle 18, attached to impeller 74. Rotor 17 is mounted for rotation about an longitudinal axis which extends both through shaft 18 and impeller 74.

The magnetic bearings for levitating rotor 17 and maintaining it in proper radial alignment with respect to its longitudinal axis are not specifically shown but may be identical to those illustrated in the pump embodiment of FIGS. 1–8 and described above.

In the FIGS. 11–14 embodiment, a first motor stator 90, comprising conductive coils or motor windings 91, is located at the rear of impeller 74. A ring of back iron 92 is located behind windings 91 and, as illustrated in FIG. 9, first motor stator 90 and back iron 92 are fixed between housing 12 and casing 14.

Figure 11:
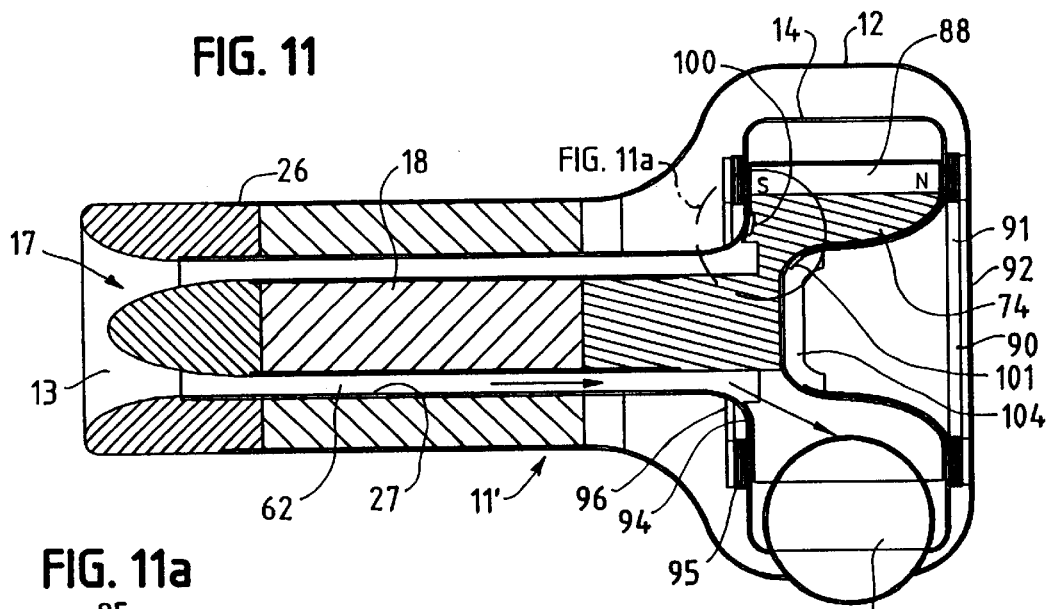
FIG. 11 is a longitudinal, cross-sectional view of a simplified, schematic representation of another embodiment of the pump.
Figure 13A:
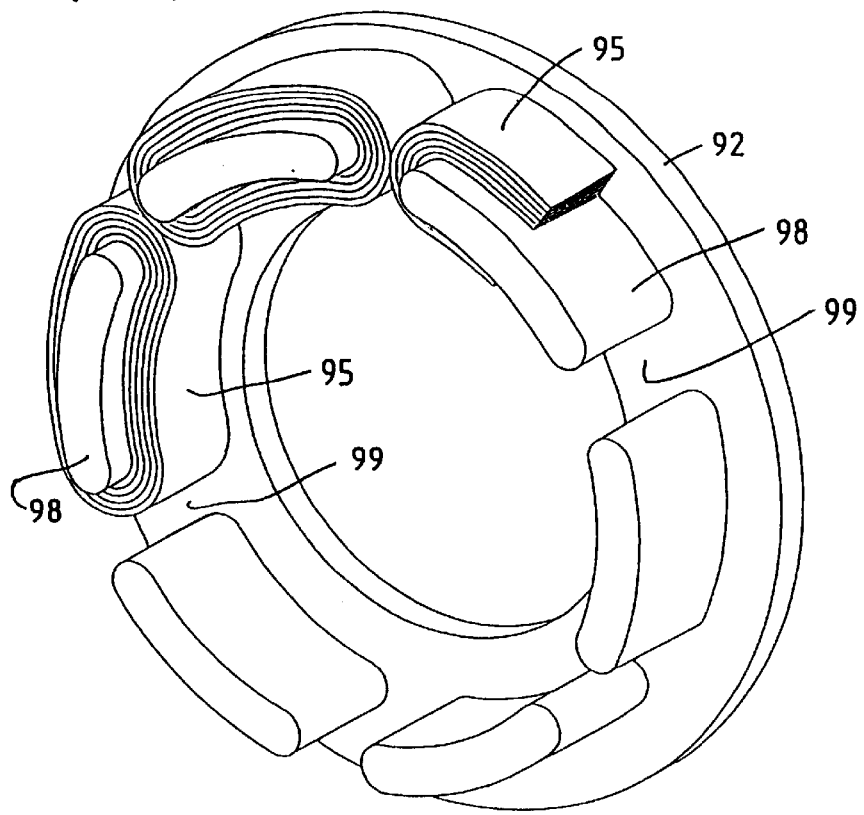
FIG. 13a is a perspective view of a portion of FIG. 13, showing the slotted motor stator.
Figure 13B:
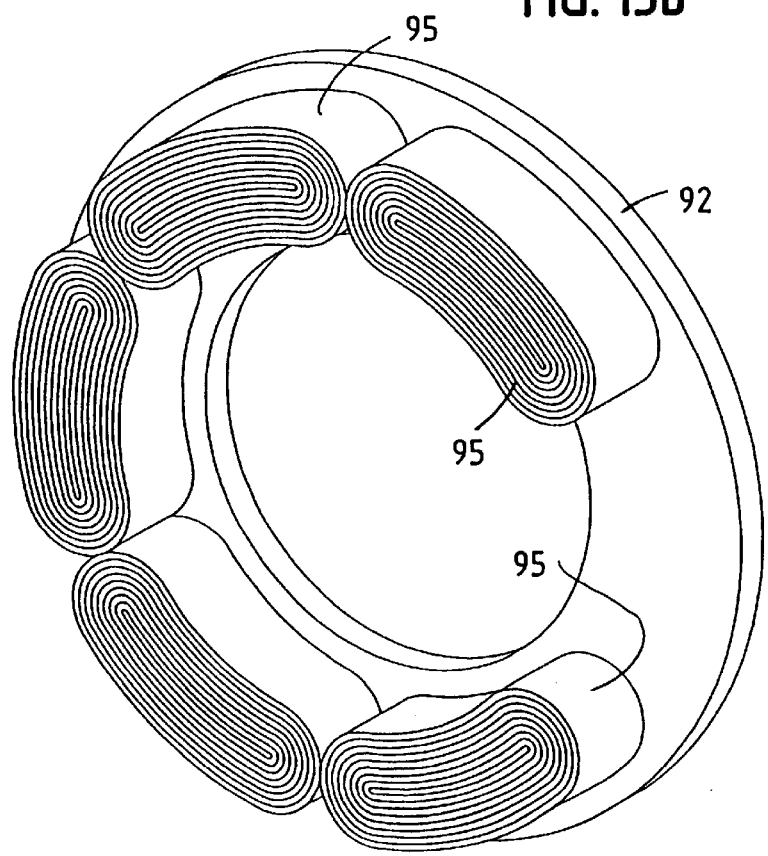
FIG. 13b is a perspective view, similar to FIG. 13a but showing a slotless motor stator.
Figure 14:
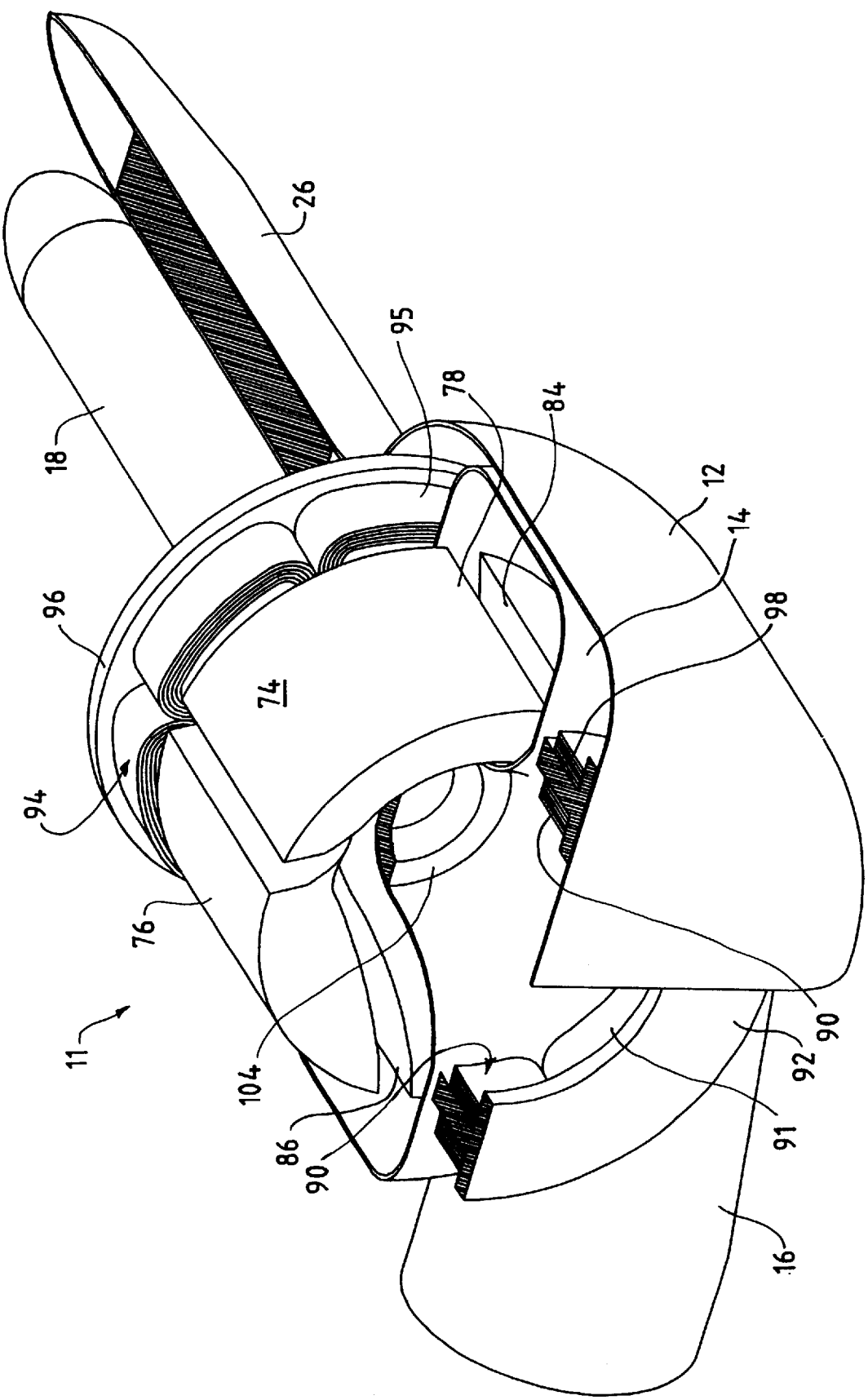
FIG. 14 is another perspective view, partially broken for clarity, of the blood pump of FIG. 11.

A second motor stator 94, comprising windings 95, is positioned on the forward side of impeller 74. As illustrated in FIG. 11, windings 95 are fixed to casing 14 and a ring of back iron 96 is positioned forward of windings 95. As illustrated in FIGS. 13, 13A and 14, back iron 92 and back iron 96 have teeth 98 15 which extend into the stator windings to form the stator iron. Thus the windings 95 wrap around the teeth 98 in the intervening slots 99 (See FIG. 13a). In the FIG. 13A embodiment, a slotless motor stator is illustrated. In that embodiment, the windings 91 are fixed to the back iron 96 and there are no teeth extending into the stator windings.

It can be seen that the motor stators 90 and 94 are placed on opposite sides of casing 14 such that each is adjacent to the pole faces of the motor rotor magnets 98. Back iron 92 and back iron 96 serve to complete a magnetic circuit. The windings 91 and 95 of the stators 90, 94 can be in series or each stator 90, 94 can be commutated independent of the other. There are several advantages to this approach:

First, as long as the pole faces of the motor rotor magnets are centered between the faces of the motor stators, the net axial force will be relatively low.

Second, the radial restoring force which results from the attractive force of the motor rotor magnets to the motor stators will be nearly twice as large as the restoring force with only one stator. The total volume and weight of the motor will be smaller than a single stator design.

Third, the dual stator design is adapted to provide system redundancy for a fail safe mode, since each stator can be made to operate independently of the other in the case of a system failure.

Figure 11A:
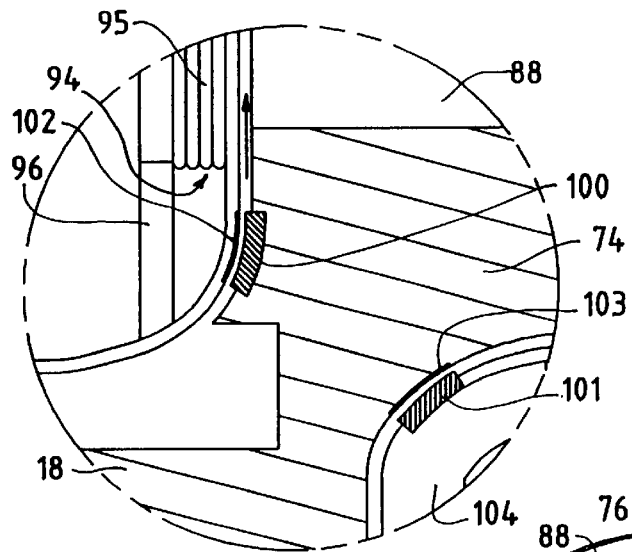
FIG. 11a is an enlarged view of the circled portion 11a from FIG. 11.
Figure 12:
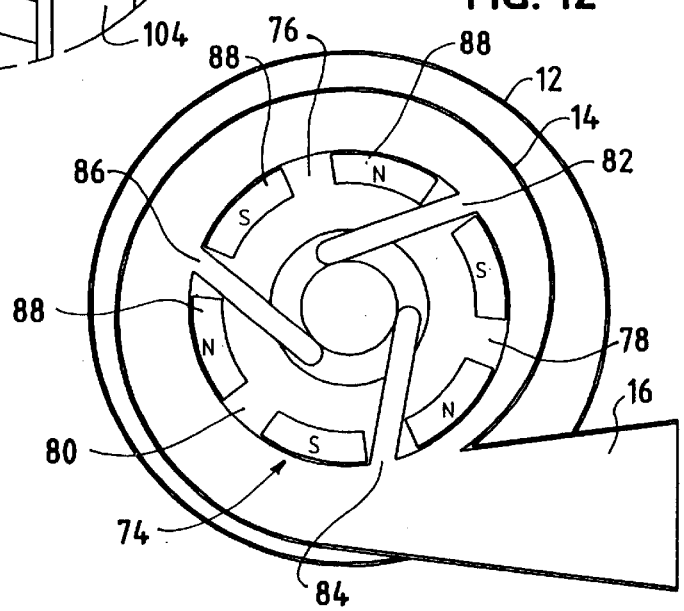
FIG. 12 is a cross-sectional end view of the FIG. 11 pump with the end of the housing and casing removed for clarity.

Fourth, hydrodynamic bearings can be located on the surface of the impeller to constrain axial motion and to provide radial support in the case of eccentric motion or shock on the device. Referring to FIGS. 11 and 11*a* in particular, hydrodynamic bearings in the form of raised pads 100, 101 and contact surfaces 102 and 103 are illustrated. Such hydrodynamic bearings are symmetrically located about the impeller as illustrated in FIG. 13, in which raised pads 100 are shown.

The raised pads could be rectangularly-shaped or wedge-shaped and are preferably formed of hardened or wear resistant materials such as ceramics, diamond coatings or titanium nitride. Alternatively, the raised pads may be formed of a different material having an alumina or other ceramic coating or insert.

The raised pads are carried by either the impeller or the casing, or an attachment to the casing. In the FIGS. 11 and 11*a* embodiment, the raised pads 100 are carried by the impeller and the raised pads 101 are carried by a cup-shaped member 104 that is fastened to the casing. Cup-shaped member 104 is utilized as a reinforcement for the casing which would not be structurally stable enough to carry the raised pads itself.

The hydrodynamic bearings are formed by a raised pad spaced from a contact surface by the blood gap. Although at rest there may be contact between the impeller and the casing, once rotation begins each hydrodynamic bearing is structured so that during relative movement between the raised pad and the contact surface the hydrodynamic action of the fluid film produces increased pressure within the bearing gap which forces the raised pad and the contact surface apart.

Depending upon the location of the hydrodynamic bearings, they can aid in axial support, radial support or both axial and radial support. For example, if the bearings are perpendicular to the rotational axis, they aid primarily in axial support but if they are at an angle with respect to the rotational axis, they aid in both radial and axial support. In the embodiment of FIGS. 11–14, the hydrodynamic bearings are positioned outside the axis of rotation, as illustrated.

Figure 15:
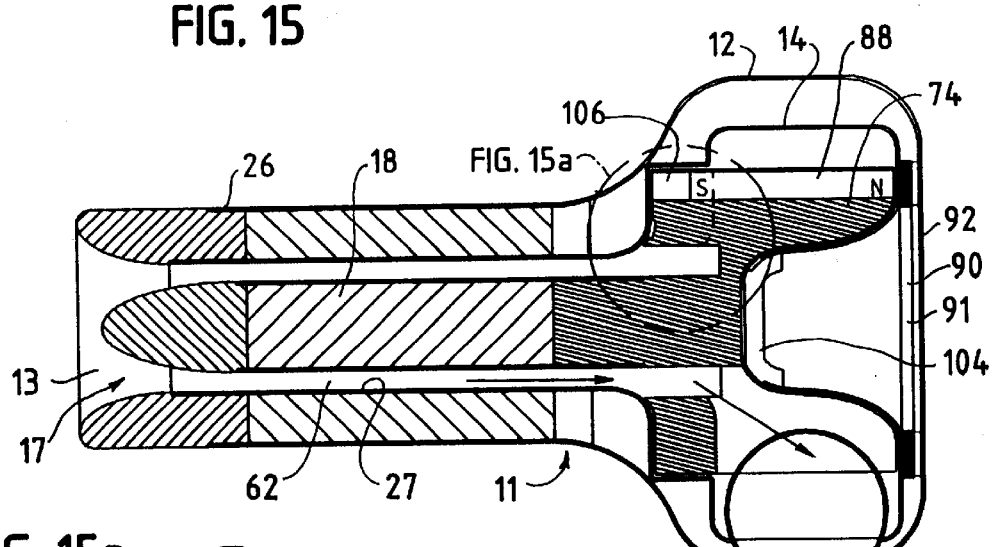
FIG. 15 is a longitudinal, cross-sectional view of another embodiment of the pump.
Figure 15A:
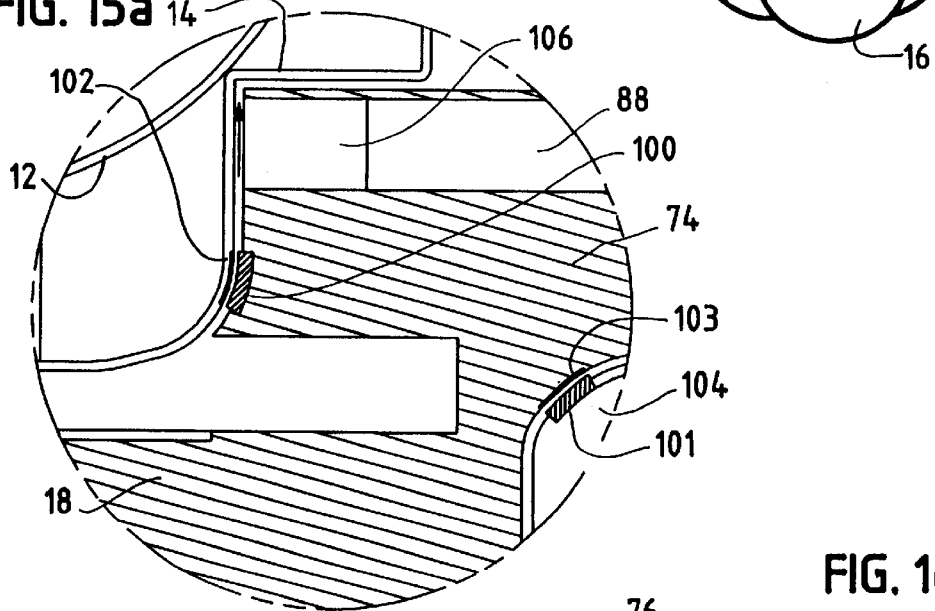
FIG. 15a is an enlarged view of the circled portion 15a from FIG. 15.
Figure 16:
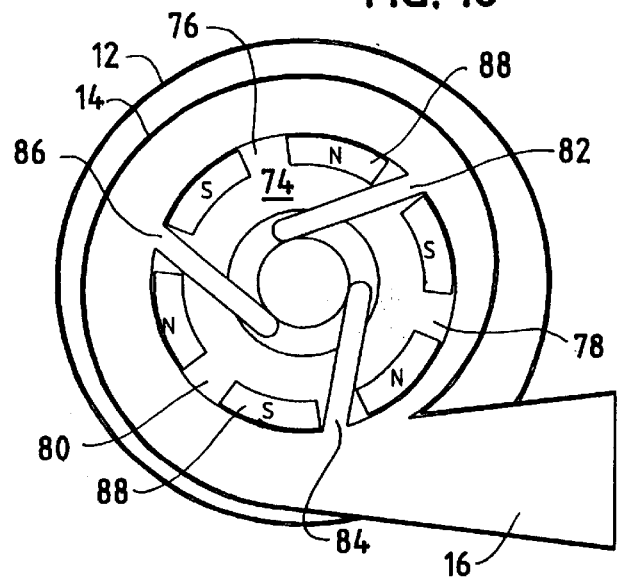
FIG. 16 is a cross-sectional end view of the FIG. 15 pump, with the end of the housing and casing removed for clarity.

In the FIGS. 15–16 embodiment, there is a single axial motor and the stator 90 is located at the rear end of impeller 74. Stator 90 comprises windings 91, and a ring of back iron 92 is located downstream of windings 91. The motor stator 90 and back iron are fixed between casing 14 and housing 12.

In the FIGS. 15–16 embodiment, a ring of back iron 106 is placed in the impeller, in axial alignment with the magnets, such that it completes the flux return path for the motor rotor magnets in the impeller. Thus while motor stator 90 and back iron 92 are located downstream of the impeller and outside of casing 12, back iron 106 is located within the impeller and within the casing 12. Using back iron to complete the magnetic circuit in this manner increases the overall efficiency of the motor.

Figure 17:
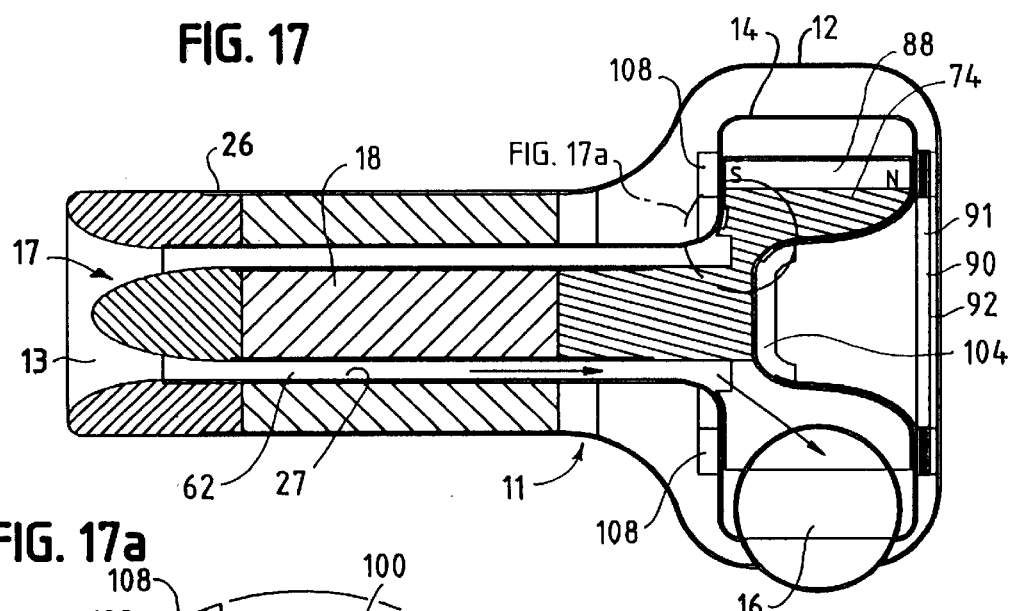
FIG. 17 is a longitudinal, cross-sectional view of another embodiment of a blood pump.
Figure 17A:
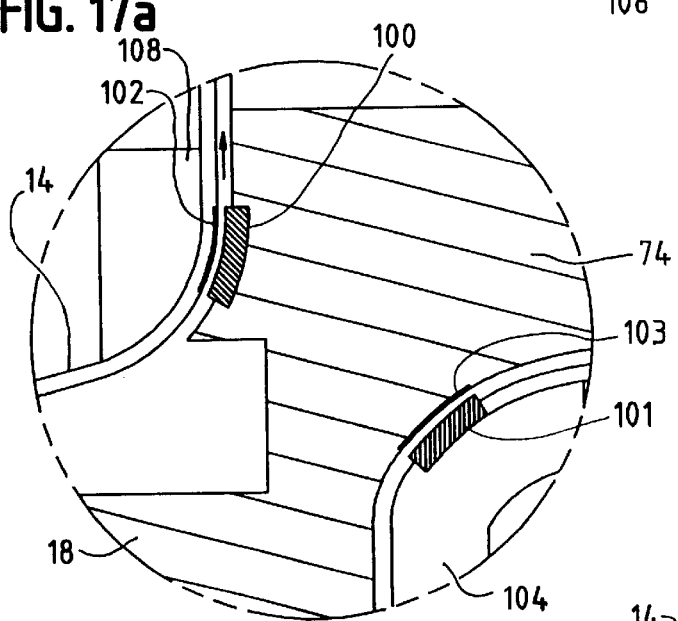
FIG. 17a is an enlarged view of the circled portion 17a from FIG. 17.
Figure 18:
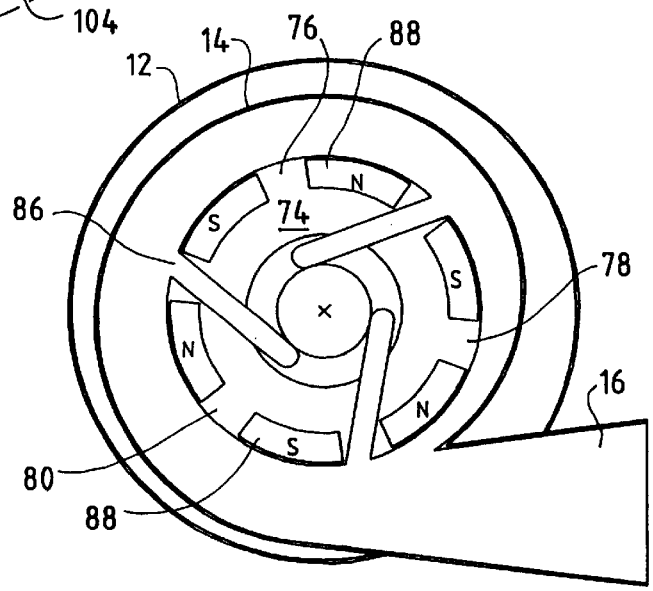
FIG. 18 is a cross-sectional end view of the FIG. 17 pump, with the end of the housing and casing removed for clarity.

Referring to the embodiment of FIGS. 17–18, a motor stator 90 and back iron 92 are provided at the rear end of impeller 74 as with the FIGS. 9–14 embodiments, but another ring of back iron 108 is placed outside pump casing 12 on the front side of the impeller and is fixed to the casing. Back iron ring 108 serves two purposes. First, it serves to help complete the flux return path for the motor rotor magnets. Second, the attractive force between the motor rotor magnets and the ring of back iron 108 substantially reduces the net axial force produced by the attraction of the motor rotor magnets for the stator iron. Third, the ring of back iron significantly increases the radial restoring force compared to just the interaction between the motor rotor magnets and the stator iron.

Figure 19:
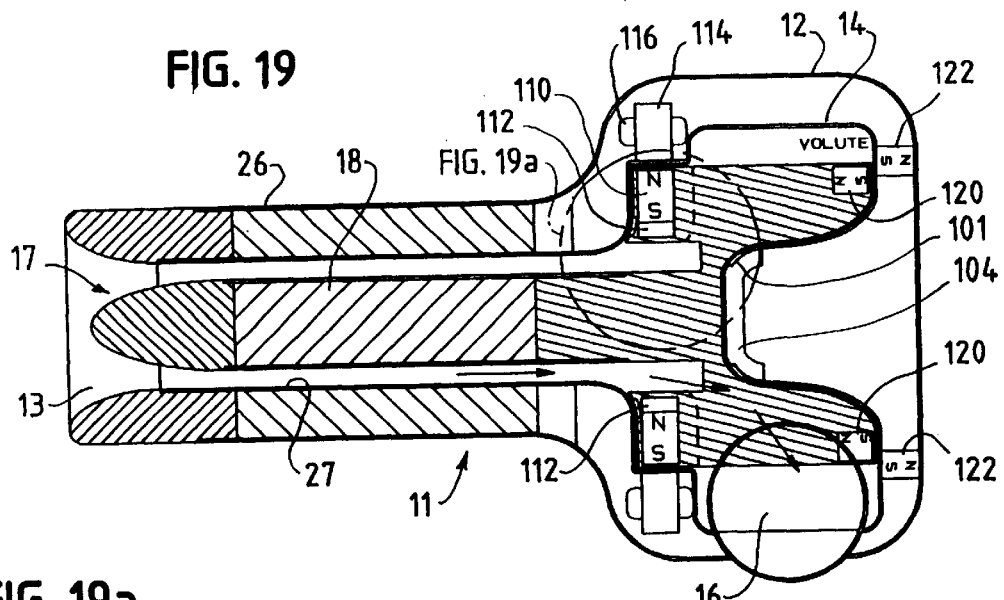
FIG. 19 is a longitudinal, cross-sectional view of another embodiment of the present invention.
Figure 19A:
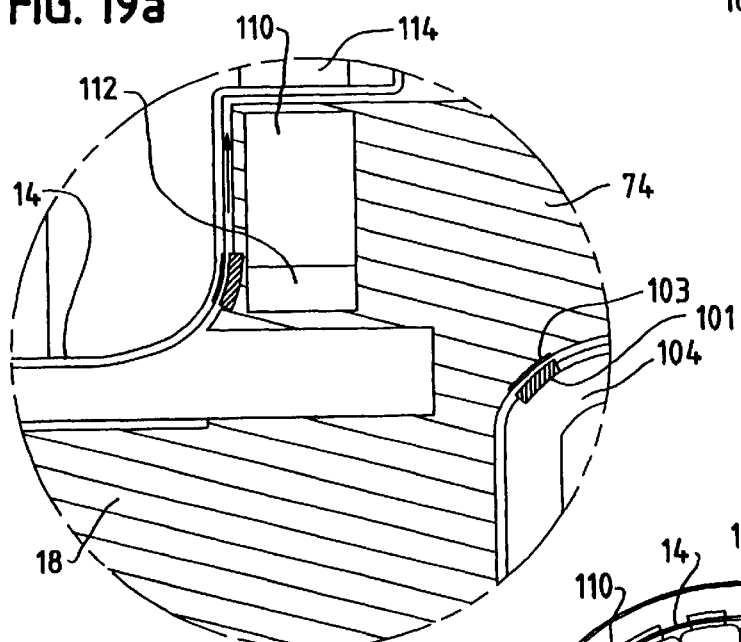
FIG. 19a is an enlarged view of the circled portion 19a from FIG. 19.
Figure 20:
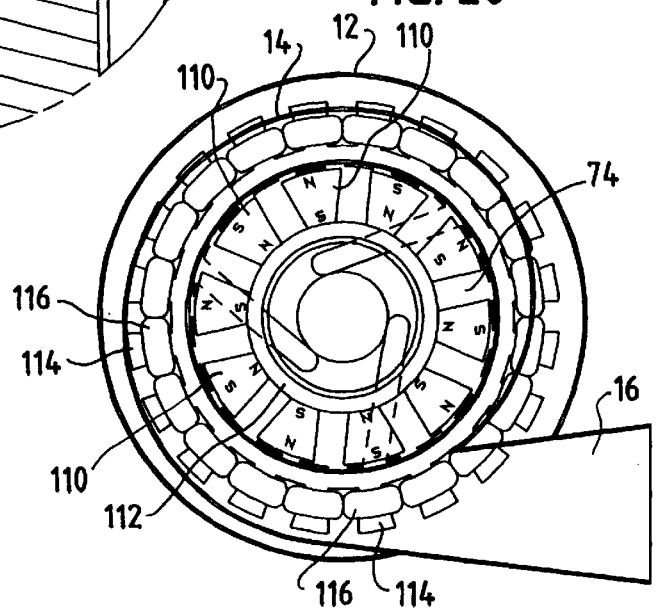
FIG. 20 is a cross-sectional end view of the FIG. 19 pump, with the end of the housing and casing removed for clarity.

Although the FIGS. 1–18 embodiments utilize an axial flux gap motor, in the FIGS. 19–20 embodiment a radial flux gap motor is utilized. To this end, a ring-shaped structure is placed on either side of the impeller to house a series of motor rotor magnets (an even number) oriented such that the magnetic poles of the motor rotor magnets are radially, and alternately, aligned. The inner diameter of the magnets is located on the surface of a ring of back iron to provide a flux return path. On the opposite end of the impeller, passive radial magnetic bearings are used.

It can be seen that in the FIGS. 19–20 embodiment the motor rotor magnets 110 are radially aligned. Radially within the motor rotor magnets 110 is a ring of back iron 112. The inner diameter of magnets 110 are located on the surface of back iron ring 112 (see FIG. 20) to provide a flux return path. The motor rotor magnets 110 and ring of back iron 112 are carried by the impeller, within the casing 14. Outside of the casing 14 there is radially positioned a ring-shaped stator 114 with motor windings 116.

A number of axial permanent magnets 120 are carried by the impeller, at its rear end. A number of axial permanent magnets 122 are fixed to the casing 14 and housing 12, downstream of and partially offset from, magnets 120. Magnets 120 and 122 serve as passive magnetic bearings for the impeller.

There are two significant differences from axial flux gap motors by using the radial flux gap motor. First, there is very little axial force produced by the interaction between the motor rotor magnets and the stator. Second, there is no restoring force with the radial flux gap motor. Radial support is provided by mechanical bearings or dedicated radial magnet bearings.

It will be appreciated, then, that I have provided an improved sealless blood pump including magnetic bearings and thrust bearing suspension to minimize thrombosis, and an impeller having a blood flow path therethrough which is calculated to minimize hemolysis.

Various elements from the FIGS. 1–8 embodiment can be used in the FIGS. 11–20 embodiments. For example, magnets 34 illustrated in FIGS. 3 and 4 could be used in impeller 74 of the FIGS. 11–20 embodiments. Also, rotor 18 of the FIGS. 11–20 embodiments could be supported using front thrust bearings such as thrust bearing 41 of the FIGS. 1–8 embodiment. Various other elements may be employed in the FIGS. 11–20 embodiments from the FIGS. 1–8 embodiment.

Although illustrative embodiments of the invention have been shown and described, it is to be understood that various modifications and substitutions may be made by those skilled in the art without departing from the novel spirit and scope of the present invention.

What is claimed is:

1. A blood pump apparatus comprising:

an impeller having a plurality of blades and a hydrodynamic bearing surface;

a plurality of magnets, each magnet disposed within one of the blades, wherein an axis of magnetization of the magnets is substantially parallel to an impeller axis of rotation.

2. The apparatus of claim 1 wherein the impeller comprises at least 3 blades.

3. The apparatus of claim 2 wherein the impeller has 4 blades.

4. The apparatus of claim 1 wherein a plurality of magnets is disposed within each blade.

5. The apparatus of claim 1 wherein a single magnet is disposed within each blade.

6. The apparatus of claim 1 wherein the blades are separated by channels extending from a first face to an opposing second face of the impeller.

7. The apparatus of claim 6 wherein the second face of the impeller includes a plurality of tapered surfaces forming the hydrodynamic bearing surface.

8. The apparatus of claim 1 wherein the apparatus further comprises:

a shaft coupled to a center of a face of the impeller, the shaft axially aligned with the impeller axis of rotation.

9. A blood pump apparatus comprising:

impeller having a hydrodynamic bearing surface and a plurality of channels extending substantially radially from a center to a periphery of the impeller; and a plurality of magnets, each magnet disposed within the impeller between a pair of channels, wherein an axis of magnetization of the magnets is substantially parallel to an impeller axis of rotation.

10. The apparatus of claim 9 wherein the impeller comprises at least 3 channels.

11. The apparatus of claim 10 wherein the impeller comprises 4 channels.

12. The apparatus of claim 9 wherein the channels extend from a first face to an opposing second face of the impeller.

13. The apparatus of claim 12 wherein the second face of the impeller includes a plurality of tapered surfaces forming the hydrodynamic bearing surface.

14. The apparatus of claim 9 wherein a plurality of magnets is disposed within each blade.

15. The apparatus of claim 9 wherein a single magnet is disposed within each blade.

16. The apparatus of claim 9 wherein the apparatus further comprises:

a shaft coupled to a center of a face of the impeller, the shaft axially aligned with the impeller axis of rotation.

17. A blood pump apparatus, comprising:

an impeller having a hydrodynamic bearing surface; and a first stator and a second stator, wherein the impeller is disposed axially between the first and second stators, wherein the impeller and stators form an axial flux gap motor.

18. The apparatus of claim 17 wherein the impeller further comprises a plurality of magnets, each magnet having a magnetic axis substantially parallel to an impeller axis of rotation.

19. The apparatus of claim 18 wherein the magnets are disposed within blades of the impeller.

20. The apparatus of the claim 18 wherein the impeller comprises a plurality of channels extending from a center to a periphery of the impeller.

21. The apparatus of claim 19 wherein a plurality of magnets is disposed within each blade.

22. The apparatus of claim 19 wherein a single magnet is disposed within each blade.

23. The apparatus of claim 20 having at least 3 channels.

24. The apparatus of the claim 20 having 4 channels.

25. A blood pump apparatus, comprising:

a housing defining a volute, and an impeller, the impeller having a hydrodynamic bearing to provide axil support, the impeller having a magnetic bearing to provide radial support.

26. The apparatus of claim 25 wherein the impeller further comprises a plurality of magnets, each magnet having a magnetic axis substantially parallel to an impeller axis of rotation.

27. The apparatus of claim 26 wherein the magnets are disposed within blades of the impeller.

28. The apparatus of claim 26 wherein the impeller comprises a plurality of channels extending from a center to a periphery of the impeller.

29. The apparatus of claim 27 wherein a plurality of magnets is disposed within each blade.

30. The apparatus of claim 27 wherein a single magnet is disposed within each blade.

31. The apparatus of claim 28 having at least 3 channels.

32. The apparatus of claim 28 having 4 channels .

* * * * *

EX PARTE REEXAMINATION CERTIFICATE (5792nd)
United States Patent
Wampler

(10) Number: US 6,234,998 C1
(45) Certificate Issued: *Jun. 26, 2007

(54) SEALLESS ROTARY BLOOD PUMP

(75) Inventor: Richard K. Wampler, Granite Bay, CA (US)

(73) Assignee: Apple Tree Partners I, L.P., New York, NY (US)

Reexamination Request:
No. 90/006,045, Jun. 28, 2001

Reexamination Certificate for:
Patent No.: 6,234,998
Issued: May 22, 2001
Appl. No.: 09/420,997
Filed: Oct. 20, 1999

(*) Notice: This patent is subject to a terminal disclaimer.

Related U.S. Application Data

(63) Continuation of application No. 09/108,434, filed on Jul. 1, 1998, now Pat. No. 6,080,133, which is a division of application No. 08/910,375, filed on Aug. 13, 1997, now Pat. No. 5,840,070, which is a continuation-in-part of application No. 08/603,536, filed on Feb. 20, 1996, now Pat. No. 5,695,471.

(51) Int. Cl.
*A61M 37/00* (2006.01)

(52) U.S. Cl. .................................................. 604/131
(58) Field of Classification Search ............ 310/156.01, 310/156.02, 156.32; 415/900; 416/223 R, 416/3; 417/353, 356, 365, 420, 423.1, 423.7, 417/423.12; 600/16; 604/131, 151; 623/3.1, 623/3.13, 3.14, 3.24
See application file for complete search history.

(56) References Cited

U.S. PATENT DOCUMENTS

| 4,944,748 A | 7/1990 | Bramm et al. |
|---|---|---|
| 5,205,721 A | 4/1993 | Isaacson |
| 5,346,458 A * | 9/1994 | Affeld .................. 600/16 |
| 5,360,445 A | 11/1994 | Goldowsky |
| 5,405,251 A * | 4/1995 | Sipin .................... 417/420 |
| 5,503,615 A | 4/1996 | Goldstein |
| 5,924,975 A | 7/1999 | Goldowsky |
| 6,071,093 A | 6/2000 | Hart |
| 6,074,180 A | 6/2000 | Khanwilkar |
| 6,100,618 A | 8/2000 | Schoeb et al. |
| 6,227,797 B1 | 5/2001 | Watterson et al. |
| 6,227,817 B1 | 5/2001 | Paden |
| 6,227,820 B1 | 5/2001 | Jarvik |
| 6,250,880 B1 | 6/2001 | Woodard et al. |
| 6,609,883 B2 | 8/2003 | Woodard |

FOREIGN PATENT DOCUMENTS

| EP | 0819330 A | 1/1998 |
|---|---|---|
| WO | WO 94/02187 | 2/1994 |

OTHER PUBLICATIONS

European Search Report, dated Dec. 8, 2004 (3 pp.).
A General Guide to the Principles, Operation and Troubleshooting of Hydrodynamic Bearings, www.kingsbury.com/hy_toc.html, Preface and Section I.

(Continued)

*Primary Examiner*—Michael J. Hayes

(57) ABSTRACT

A implantable rotary sealless blood pump is provided. The pump includes a housing having an inlet tube on one end and an impeller casing on the other end. A rotor is mounted for rotation within the housing, with the rotor having an elongated shaft portion and an impeller attached to the shaft portion. The impeller is located within the impeller casing. Radial magnetic bearings are carried by the shaft portion and radial magnetic bearings are carried by the housing for maintaining the shaft portion of the rotor within the inlet tube of the housing. A rotor motor includes a plurality of permanent magnets carried by the impeller and a motor stator includes an electrically conductive coil located within the housing. A ring of back iron is carried by the impeller to aid in completing a flux return path for the permanent magnets. A plurality of hydrodynamic thrust bearings are located outside of the axis of rotation of the rotor. The impeller uses large axially thick blade sectors with narrow blood channels extending through the impeller, to minimize hemolysis and to increase the working surface of the blades.

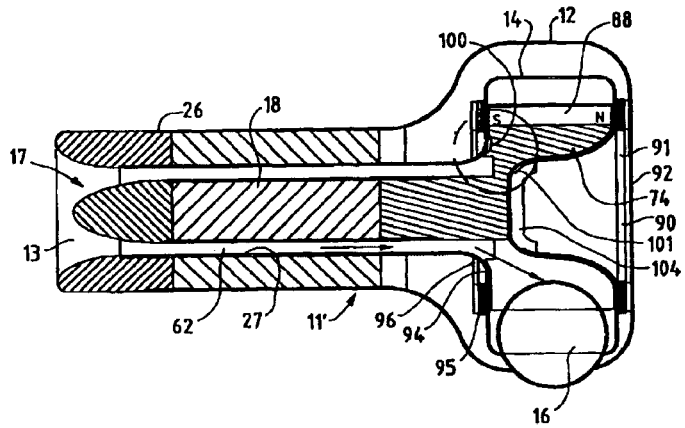

OTHER PUBLICATIONS

Lubrication of Bearings by E. I. Radzimovsky, The Ronald Press Company, cover and pps. 6–7 and 49–57.
Hart, R. et al., "A Magnetically Suspended Implantable Centrifugal Blood Pump," *3rd Congress of the International Society of Rotary Blood Pumps*, Houston, No. 36 (Aug. 24–27 1995); Abstract Only.
Yonnet, J.P., "Permanent Magnet Bearings and Couplings," *IEEE Transactions on Magnetics*, vol. MAG–17, No. 1, 1169–1173 (1981).
"A Magnetically Suspended Implantable Centrifugal Pump" Robert M. Hart, Victor G. Filipenco, Robert T. V. Kung, 3rd Congress of the International Society for Rotary Blood Pumps, Houston, 6 viewgraphs, Aug. 1995.
"A Magnetically Suspended and Hydrostatically Stabilized Centrifugal Blood Pump", Robert M. Hart, Victor G. Filipenko, and Robert T.V. Kung, Artificial Organs, 20(6):591–596, Jun. 1996.
"Design considerations for Bearingless Rotary Pumps", Robert T.V. Kung and Robert M. Hart, Artificial Organs 21(7):645–650, Jul. 1997.
Schima, H. et al., "An Implantable Seal–less Centrifugal Pump with Integrated Double–Disk Motor" Artificial Organs, 19(7) 639–643, Jul. 1995.
Yamane, T. et al., "Design of a Centrifugal Blood Pump with Magnetic Suspension," Artificial Organs, 19(7), 625–630, Jul. 1995.
Proceedings of the Third Congress of the International Society for Rotary Blood Pumps, (ISRP), Houston Texas, Aug. 24–27, 1995, published in Artificial Organs, vol. 20, No. 6, Jun. 1996.
Khanwilkar, Pratap et al., "Using Hybrid Magnetic Bearings to Completely Suspend the Impeller of a Ventricular Assist Device," Artificial Organs 20(6):597–604 (1996).
Tamaka et al., "A New Seal–less Centrifugal Blood Pump", Japan Journal of Artifical Organs, 14 (3), pp. 1126–1129, (1985).
Nishida et al., "Development of the Terumo Capiox Centrifugal Pump and Its Clinical Application to Open Heart Surgery: A Comparative Study with the Roller Pump", pp. 24–28, (1992).
Kijima et al., "A Straight Path Centrifugal Blood Pump Concept in the Capiox Centrifugal Pump", pp. 32–37, (1993).
Yamane et al. "Fundamental Characteristics of Magnetically Suspended Centrifugal Blood Pump", pp. 130–131 (1994).
Kijima et al., "The Margin of Safety in the Use of a Straight Path Centrifugal Blood Pump", *Artifical Organs*, 18(9), pp. 680–686, (1994).
"Implantable Artifical Cardiac Blood Pump Prototype Developed", Medical Equipment Journal of Japan, (May 1994).
Yamane et al., "Design of a Centrifugal Blood Pump with Magnetic Suspension", 1 page, Abstract, (Sep. 1994).
Yamane et al., "Design of a Centrifugal Blood Pump with Magnetic Suspension", *Artifical Organs*, 19(7) pp. 625–630, (1995).
Akamatsu et al., "Recent Studies of the Centrifugal Blood Pump with a Magnetically Suspended Impeller", *Artificial Organs*, 19(7), pp. 631–634, (1995).
Yamane "Performance Improvements of a Centrifugal Blood Pump with Mono–Pivot Magnetic–Suspension", pp. 538–539, (1996).
Kim et al., "In Vitro Characterization of a Magnetically Suspended Continuous Flow Venticular Assist Device," 4535 ASAIO Journal, 41 (1995) July./Sept. No. 3.
C. Peter Cho et al.; Eddy Current Loss Calculation in the Permanent Magnet of a Large Horse Power Axial–Field Motor; Jun. 14, 1994; Proceedings, Twenty–third Annual Symposium, Incremental Motion Control Systems & Devices, pp. 245–253.
C. Peter Cho et al.; Cogging Torque Reduction, Axial Force Variation, and Output Torque Effect of a High–Power Density, Axial Field, Brushless, Permanent Magnet Motor; Jun. 6, 1995; Proceedings, Twenty–fourth Annual Symposium, Incremental Motion Control Systems & Devices, pp. 297–307.
C. Peter Cho et al.; Feasibility Study of a Novel Integrated Electric Motor/Pump for Underwater Applications; Jun. 6, 1995; Proceedings, Twenty–fourth Annual Symposium, Incremental Motion Control Systems & Devices, pp. 309–316.
C. Peter Cho. et al.; Ongoing Feasibility Study of a Novel Integrated Electric Motor/Pump Concept; Jun. 11, 1996; Proceedings, Twenty–fifth Annual Symposium, Incremental Motion Control Systems & Devices, pp. 51–62.
C. Peter Cho. et al.; Energy Losses in Magnetic Lamination Materials of a Novel Integrated Motor/Pump System; Jul. 22, 1997; Proceedings, Twenty–sixth Annual Symposium, Incremental Motion Control System & Devices, pp. 325–333.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 9, 17 and 25 are determined to be patentable as amended.

Claims 2-6, 7, 8, 10-16, 18-24 and 26-32, dependent on an amended claim, are determined to be patentable.

1. A blood pump apparatus comprising:
   an impeller having a plurality of blades and a hydrodynamic bearing surface *disposed for exposure to blood being pumped*;
   a plurality of magnets, each magnet disposed within one of the blades, wherein an axis of magnetization of the magnets is substantially parallel to an impeller axis of rotation.

9. A blood pump apparatus comprising:
   *an* impeller having a hydrodynamic bearing surface *disposed for exposure to blood being pumped* and a plurality of channels extending substantially radially from a center to a periphery of the impeller; and
   a plurality of magnets, each magnet disposed within the impeller between a pair of channels, wherein an axis of magnetization of the magnets is substantially parallel to an impeller axis of rotation.

17. A blood pump apparatus, comprising:
    an impeller having a hydrodynamic bearing surface *disposed for exposure to blood being pumped*; and
    a first stator and a second stator, wherein the impeller is disposed axially between the first and second stators, wherein the impeller and stators form an axial flux gap motor.

25. A blood pump apparatus, comprising:
    a housing defining a volute, and
    an impeller, the impeller having a hydrodynamic bearing *disposed for exposure to blood being pumped* to provide [axil] *axial* support, the impeller having a magnetic bearing to provide radial support.

* * * * *